US009700551B2

(12) United States Patent
Alisi et al.

(10) Patent No.: US 9,700,551 B2
(45) Date of Patent: Jul. 11, 2017

(54) USE OF 1H-INDAZOLE-3-CARBOXAMIDE COMPOUNDS AS GLYCOGEN SYNTHASE KINASE 3 BETA INHIBITORS

(71) Applicant: AZIENDE CHIMICHE RIUNITE ANGELINI FRANCESCO A.C.R.A.F. S.P.A., Rome (IT)

(72) Inventors: Maria Alessandra Alisi, Rome (IT); Nicola Cazzolla, Rome (IT); Barbara Garofalo, Rome (IT); Guido Furlotti, Rome (IT); Gabriele Magaro', Rome (IT); Rosella Ombrato, San Lorenzo Del Vallo (IT); Francesca Mancini, Rome (IT)

(73) Assignee: AZIENDE CHIMICHE RIUNITE ANGELINI FRANCESCO A.C.R.A.F. S.P.A., Rome (IT)

( * ) Notice: Subject to any disclaimer, the term of this patent is extended or adjusted under 35 U.S.C. 154(b) by 0 days.

(21) Appl. No.: 14/825,261

(22) Filed: Aug. 13, 2015

(65) Prior Publication Data
US 2016/0045485 A1 Feb. 18, 2016

Related U.S. Application Data

(63) Continuation of application No. 14/373,393, filed as application No. PCT/EP2013/052523 on Feb. 8, 2013, now Pat. No. 9,163,013.

(30) Foreign Application Priority Data

Feb. 21, 2012 (EP) .................................... 12156298

(51) Int. Cl.
| A61K 31/454 | (2006.01) |
| A61K 31/4545 | (2006.01) |
| A61K 31/5377 | (2006.01) |
| C07D 401/14 | (2006.01) |
| C07D 405/14 | (2006.01) |
| C07D 413/14 | (2006.01) |
| C07D 401/12 | (2006.01) |
| C07D 417/14 | (2006.01) |

(52) U.S. Cl.
CPC ........ *A61K 31/454* (2013.01); *A61K 31/4545* (2013.01); *A61K 31/5377* (2013.01); *C07D 401/12* (2013.01); *C07D 401/14* (2013.01); *C07D 405/14* (2013.01); *C07D 413/14* (2013.01); *C07D 417/14* (2013.01)

(58) Field of Classification Search
None
See application file for complete search history.

(56) References Cited

U.S. PATENT DOCUMENTS

| 5,945,434 | A | 8/1999 | Suzuki et al. | |
| 6,096,746 | A | 8/2000 | Suzuki et al. | |
| 6,197,769 | B1 * | 3/2001 | Alisi | C07D 401/12 514/234.5 |
| 8,415,476 | B2 * | 4/2013 | Alisi | C07D 231/56 546/229 |
| 8,455,519 | B2 | 6/2013 | Alisi et al. | |
| 9,163,013 | B2 * | 10/2015 | Alisi | C07D 401/14 |
| 2006/0052417 | A1 | 3/2006 | Alisi et al. | |
| 2007/0010555 | A1 | 1/2007 | Alisi et al. | |
| 2010/0048907 | A1 | 2/2010 | Alisi et al. | |
| 2010/0094015 | A1 | 4/2010 | Alisi et al. | |
| 2011/0112161 | A1 | 5/2011 | Bolin et al. | |
| 2015/0057294 | A1 | 2/2015 | Alisi et al. | |

FOREIGN PATENT DOCUMENTS

| EP | 0 829 474 A1 | 3/1998 |
| WO | WO 94/10174 A1 | 5/1994 |
| WO | WO 2004/014864 A1 | 2/2004 |
| WO | WO 2004/074275 A1 | 9/2004 |
| WO | WO 2004/101548 A1 | 11/2004 |
| WO | WO 2010/109005 A1 | 9/2010 |

OTHER PUBLICATIONS

International Search Report issued Mar. 12, 2013 in PCT/EP2013/052523.
Francesco Benedetti et al., "A glycogen synthase kinase 3β promoter gene single nucleotide polymorphism is associated with age at onset and response to total sleep deprivation in bipolar depression", Neuroscience Letters, 368, (2004), pp. 123-126.
Carol A. Grimes, et al., "The multifaceted roles of glycogen synthase kinase 3β in cellular signaling", Progress in Neurobiology 65, (2001), pp. 391-426, www.elsevier.com/locate/pneurobio.
Noor Embi, et al., "Glycogen Synthase Kinase-3 from Rabbit Skeletal Muscle Separation from Cyclic-AMP-Dependent Protein Kinase and Phosphorylase Kinase", Eur. J. Biochem. 107, (1980), pp. 519-527.
Philip Cohen, et al., "PDKI, one of the missing links in insulin signal transduction?", The Tenth Datta Lecture, FEBS 18635, FEBS Letters, 410, (1997), pp. 3-10.
Betsy B. Dokken, et al., "Acute selective glycogen synthase kinase-3 inhibition enhances insulin signaling in prediabetic insulin-resistant rat skeletal muscle", Am. J. Physiol. Endocrinol Metab. 288, 2005, pp. E1188-E1194, http://www.ajpendo.org.
David B. Ring, et al., "Selective Glycogen Synthase Kinase 3 Inhibitors Potentiate Insulin Activation of Glucose Transport and Utilization In Vitro and In Vivo", Diabetes, vol. 52, Mar. 2003, 8 pages.

(Continued)

*Primary Examiner* — Samantha Shterengarts
(74) *Attorney, Agent, or Firm* — Oblon, McClelland, Maier & Neustadt, L.L.P.

(57) ABSTRACT

The present invention relates to the new use of 1H-indazole-3-carboxamide compounds as glycogen synthase kinase 3 beta (GSK-3β) inhibitors and to their use in the treatment of GSK-3β-related disorders such as, for example, (i) insulin-resistance disorders; (ii) neurodegenerative diseases; (iii) mood disorders; (iv) schizophrenic disorders; (v) cancerous disorders; (vi) inflammation, (vii) substance abuse disorders; and (viii) epilepsies.

21 Claims, No Drawings

(56) References Cited

OTHER PUBLICATIONS

Diane P. Hanger, et al.,"Glycogen synthase kinase-3 induces Alzheimer's disease-like phosphorylation of tau: generation of paired helical filament epitopes and neuronal localisation of the kinase", Neuroscience Letters, 147, (1992), pp. 58-62.

Ming Hong, et al., "Insulin and Insulin-like Growth Factor-1 Regulate Tau Phosphorylation in Cultured Human Neurons", The Journal of Biological Chemistry, vol. 272, No. 31, Issue of Aug. 1, 1997, pp. 19547-19553.

A. Cedazo-Minguez, et al.,"Apolipoprotein E and β-amyloid (1-42) regulation of glycogen synthase kinase-3β", Journal of Neurochemistry, 2003 International Society for Neurochemistry, 2003, 87, pp. 1152-1164.

Tetyana Duka, et al., α-Synuclein contributes to GSK-3β-catalyzed Tau phosphorylation in Parkinson's disease models The FASEB Journal • Research Communication, vol. 23, Sep. 2009, pp. 2820-2830m, www.fasebj.org.

Geetha Vani Rayasam, et al., "Glycogen synthase kinase 3: more than a namesake", British Journal of Pharmacology (2009), 156, pp. 885-898, http://www.brjpharmacol.org/.

Michael P. Mazanetz, et al., "Untangling tau hyperphosphorylation in drug design for neurodegenerative diseases", 464, Jun. 2007, vol. 6, Nature Reviews, Nature Publishing Group, pp. 464-479, www.nature.com/reviews/drugdisc.

Félix Hernández, et al., "The role of glycogen synthase kinase 3 in the early stages of Alzheimers disease", Minireview, FEBS Letters, 582, (2008), pp. 3848-3854.

Laurent Meijer, et al., "Pharmacological inhibitors of glycogen synthase kinase 3", Trends in Pharmacological Sciences vol. 25, No. 9 Sep. 2004, pp. 471-480, http://www.sciencedirect.com/.

J. Calderó, et al., "Lithium prevents excitotoxic cell death of motoneurons in organotypic slice cultures of spinal cord", Neuroscience, 165, (2010), pp. 1353-1369.

Todd D. Gould, "Targeting glycogen synthase kinase-3 as an approach to develop novel mood-stabilising medications", Central & Peripheral Nervous Systems, Review, Expert Opin. Ther. Targets, (2006), 10(3), pp. 377-392.

Ludwig Rinnab, et al., "Inhibition of Glycogen Synthase Kinase-3 in Androgen-Responsive Prostate Cancer Cell Lines: Are GSK Inhibitors Therapeutically Useful?", Neoplasia, vol. 10, No. 6, Jun. 2008, pp. 624-633 www.neoplasia.com.

Qi Cao, et al., "Glycogen synthase kinase-3β positively regulates the proliferation of human ovarian cancer cells", Cell Research, 2006, 16, pp. 671-677 www.nature.com/cr.

Noah W. Birch, et al. "Glycogen Synthase Kinase-3 and Leukemia: Restoring the Balance", Cancer Cell 17, Jun. 15, 2010, 2010 Elsevier Inc. pp. 529-531.

Hannes Lohi, et al., "Novel glycogen synthase kinase 3 and ubiquitination pathways in progressive myoclonus epilepsy", Human Molecular Genetics, 2005, vol. 14, No. 18, pp. 2727-2736.

Rajat Puri, et al., "Protein Synthesis, Post-Translational Modification, and Degradation: Hyperphosphorylation and Aggregation of Tau in Laforin-deficient Mice, an Animal Model for Lafora Disease", The Journal of Biological Chemistry 2009, 284, pp. 22657-22663.

S Phukan, et al. "GSK3β: role in therapeutic landscape and development of modulators", (BJP) British Journal of Pharmacology 2010, 160, pp. 1-19.

Laurent Meijer, et al., "GSK-3-Selective Inhibitors Derived from Tyrian Purple Indirubins", Chemistry & Biology, vol. 10, Dec. 2003, pp. 1255-1266.

Bertrand Léger, PhD, et al., "Atrogin-1, MuRF1, and FoXo, as well as phosphorylated GSK-3β and 4E-BP1 are reduced in skeletal muscle of chronic spinal cord-injured patients" Muscle Atrophy in SCI, Patients Muscle & Nerve, Jul. 2009, pp. 69-78.

Daniela Galimberti, et al., "GSK3β genetic variability in patients with Multiple Sclerosis", Neuroscience Letters, 497, 2011, pp. 46-48.

Richard S. Jope, et al., "Glycogen Synthase Kinase-3 (GSK3) in Psychiatric Diseases and Therapeutic Interventions", Current Drug Targets, 2006, 7, pp. 1421-1434.

Guang Chen, et al., "The Mood-Stabilizing Agent Valproate Inhibits the Activity of Glycogen Synthase Kinase-3", Journal of Neurochemistry, 1999 International Society for Neurochemistry, J. Neurochem. 72, 1999, pp. 1327-1330.

Peter S. Klein, et al., "A molecular mechanism for the effect of lithium on development", Proc. Natl. Acad. Sci. USA vol. 93, Aug. 1996, Developmental Biology, pp. 8455-8459.

Effat S. Emamian, et al., "Convergent evidence for impaired AKT1-GSK3β signaling in schizophrenia", Nature Genetics, vol. 36, No. 2, Feb. 2004, pp. 131-137, http://www.nature.com/naturegenetics.

Jia Luo, et al., "Glycogen synthase kinase 3β(GSK3β) in tumorigenesis and cancer chemotherapy", Cancer Letters, Cancer Letters, 273, 2009, pp. 194-200, journal homepage: www.elsevier.com/locate/canlet.

G. Garcea, et al., "Glycogen Synthase Kinase-3 Beta; A New Target in Pancreatic Cancer?", Current Cancer Drug Targets, 2007, vol. 7, No. 3, pp. 209-215.

Jagadish C. Ghosh, et al., "Activation of p53-Dependent Apoptosis by Acute Ablation of Glycogen Synthase Kinase-3 β in Colorectal Cancer Cells", Clinical Cancer Research, Cancer Therapy: Preclinical, 2005, 11, pp. 4580-4588.

G. Klamer, et al., "Using Small Molecule GSK3β Inhibitors to Treat Inflammation", Current Medicinal Chemistry, 2010, 17, pp. 2873-2881.

Huizhi Wang, et al., "Glycogen synthase kinase 3: A point of convergence for the host inflammatory response", Cytokine 53, 2011, Cytokine, pp. 130-140.

Jonathan S. Miller, et al., "Cocaine-induced hyperactivity and sensitization are dependent on GSK3", Neuropharmacology, 56, 2009, pp. 1116-1123.

Daniel F. Martins, et al., "The Antinociceptive Effects of AR-A014418, a Selective Inhibitor of Glycogen Synthase Kinase-3 Beta, in Mice", The Journal of Pain, vol. 12, No. 3, Mar. 201, pp. 315-322 http://www.sciencedirect.com/.

\* cited by examiner

SEQUENCE LISTING

<160> NUMBER OF SEQ ID NOS: 1

<210> SEQ ID NO 1
<211> LENGTH: 18
<212> TYPE: PRT
<213> ORGANISM: Artificial Sequence
<220> FEATURE:
<223> OTHER INFORMATION: Synthetic substrate peptide for phosphorylation
      assay
<220> FEATURE:
<221> NAME/KEY: MOD_RES
<222> LOCATION: (1)..(1)
<223> OTHER INFORMATION: ULight dye directly labeling this residue

<400> SEQUENCE: 1

Cys Phe Phe Lys Asn Ile Val Thr Pro Arg Thr Pro Pro Pro Ser Gln
1               5                   10                  15

Gly Lys

USE OF 1H-INDAZOLE-3-CARBOXAMIDE COMPOUNDS AS GLYCOGEN SYNTHASE KINASE 3 BETA INHIBITORS

CROSS REFERENCE TO RELATED APPLICATIONS

This application is a continuation of U.S. patent application Ser. No. 14/373,393, filed Jul. 21, 2014; which is a 371 of PCT/EP2013/052523, filed Feb. 8, 2013, the disclosures of which are incorporated herein by reference in their entireties. This application claims priority to European Patent Application No. 12156298.7, filed Feb. 21, 2012, the disclosure of which is incorporated herein by reference in its entirety.

FIELD OF THE INVENTION

The present invention relates to the new use of 1H-indazole-3-carboxamide compounds acting as glycogen synthase kinase 3 beta (GSK-3β) inhibitors and to their use in the treatment of GSK-3β-related disorders such as (i) insulin-resistance disorders; (ii) neurodegenerative diseases; (iii) mood disorders; (iv) schizophrenic disorders; (v) cancerous disorders; (vi) inflammation, (vii) substance abuse disorders; and (viii) epilepsies.

STATE OF THE ART

Protein kinases constitute a large family of structurally related enzymes, which transfer phosphate groups from high-energy donor molecules (such as adenosine triphosphate, ATP) to specific substrates, usually proteins. After phosphorylation, the substrate undergoes to a functional change, by which kinases can modulate various biological functions.

In general, protein kinases can be divided in several groups, according to the substrate that is phosphorylated. For example, serine/threonine kinase phosphorylates the hydroxyl group on the side chain of serine or threonine aminoacid.

Glycogen synthase kinases 3 (GSK-3) are constitutively active multifunctional enzymes, quite recently discovered, belonging to the serine/threonine kinases group.

Human GSK-3 are encoded by two different and independent genes, which leads to GSK-3α and GSK-3β proteins, with molecular weights of about 51 and 47 kDa, respectively. The two isoforms share nearly identical sequences in their kinase domains, while outside of the kinase domain, their sequences differ substantially (Benedetti et al., *Neuroscience Letters*, 2004, 368, 123-126). GSK-3α is a multifunctional protein serine kinase and GSK-3β is a serine-threonine kinase.

It has been found that GSK-3β is widely expressed in all tissues, with widespread expression in the adult brain, suggesting a fundamental role in neuronal signaling pathways (Grimes and Jope, *Progress in Neurobiology*, 2001, 65, 391-426). Interest in glycogen synthase kinases 3 arises from its role in various physiological pathways, such as, for example, metabolism, cell cycle, gene expression, embryonic development oncogenesis and neuroprotection (Geetha et al., *British Journal Pharmacology*, 2009, 156, 885-898).

GSK-3β was originally identified for its role in the regulation of glycogen synthase for the conversion of glucose to glycogen (Embi et *Eur J Biochem*, 1980, 107, 519-527). GSK-3β showed a high degree of specificity for glycogen synthase.

Type 2 diabetes was the first disease condition implicated with GSK-3β, due to its negative regulation of several aspects of insulin signaling pathway. In this pathway 3-phosphoinositide-dependent protein kinase 1 (PDK-1) activates PKB, which in turn inactivates GSK-3β. This inactivation of GSK-3β leads to the dephosphorylation and activation of glycogen synthase, which helps glycogen synthesis (Cohen et al., *FEBS Lett.*, 1997, 410, 3-10). Moreover, selective inhibitors of GSK-3β are expected to enhances insulin signaling in prediabetic insulin-resistant rat skeletal muscle, thus making GSK-3β an attractive target for the treatment of skeletal muscle insulin resistance in the pre-diabetic state (Dokken et al., *Am J. Physiol. Endocrinol. Metab.*, 2005, 288, E1188-E1194).

GSK-3β was also found to be a potential drug target in others pathological conditions due to insulin-resistance disorders, such as syndrome X, obesity and polycystic ovary syndrome (Ring D B et al., *Diabetes*, 2003, 52: 588-595).

It has been found that GSK-3β is involved in the abnormal phosphorylation of pathological tau in Alzheimer's disease (Hanger et al., *Neurosci. Lett.*, 1992, 147, 58-62; Mazanetz and Fischer, *Nat Rev Drug Discov.*, 2007, 6, 464-479; Hong and Lee, *J. Biol. Chem.*, 1997, 272, 19547-19553). Moreover, it was proved that early activation of GSK-3β, induced by apolipoprotein ApoE4 and β-amyloid, could lead to apoptosis and tau hyperphosphorylation (Cedazo-Minguez et al., *Journal of Neurochemistry*, 2003, 87, 1152-1164). Among other aspect of Alzheimer's disease, it was also reported the relevance of activation of GSK-3β at molecular level (Hernandez and Avila, *FEBS Letters*, 2008, 582, 3848-3854).

Moreover, it was demonstrated that GSK-3β is involved in the genesis and maintenance of neurodegenerative changes associated with Parkinson's disease (Duka T. et al., *The FASEB Journal*, 2009; 23, 2820-2830).

Accordingly to these experimental observations, inhibitors of GSK-3β may find applications in the treatment of the neuropathological consequences and the cognitive and attention deficits associated with tauopathies; Alzheimer's disease; Parkinson's disease; Huntington's disease (the involvement of GSK-3β in such deficits and diseases is disclosed in Meijer L. et al., *TRENDS Pharm Sci*, 2004; 25, 471-480); dementia, such as, but not limited to, vascular dementia, post-traumatic dementia, dementia caused by meningitis and the like; acute stroke; traumatic injuries; cerebrovascular accidents; brain and spinal cord trauma; peripheral neuropathies; retinopathies and glaucoma (the involvement of GSK-3β in such conditions is disclosed in WO 2010/109005).

The treatment of spinal neurodegenerative disorders, like amyotrophic lateral sclerosis, multiple sclerosis, spinal muscular atrophy and neurodegeneration due to spinal cord injury has been also suggested in several studies related to GSK-3β inhibition, such as, for example in Calderó J. et al., "Lithium prevents excitotoxic cell death of motoneurons in organotypic slice cultures of spinal cord", Neuroscience. 2010 Feb. 17; 165(4):1353-69, Léger B. et al., "Atrogin-1, MuRF1, and FoXO, as well as phosphorylated GSK-3beta and 4E-BP1 are reduced in skeletal muscle of chronic spinal cord-injured patients", Muscle Nerve, 2009 July; 40(1):69-78, and Galimberti D. et al., "GSK3β genetic variability in patients with Multiple Sclerosis", Neurosci Lett. 2011 Jun. 15; 497(1):46-8.

Furthermore, GSK-3β has been linked to the mood disorders, such as bipolar disorders, depression, and schizophrenia.

Inhibition of GSK-3β may be an important therapeutic target of mood stabilizers, and regulation of GSK-3β may be involved in the therapeutic effects of other drugs used in psychiatry. Dysregulated GSK-3β in mood disorder, bipolar disorder, depression and schizophrenia could have multiple effects that could impair neural plasticity, such as modulation of neuronal architecture, neurogenesis, gene expression and the ability of neurons to respond to stressful, potentially lethal conditions (Jope and Roh, *Curr. Drug Targets*, 2006, 7, 1421-1434).

The role of GSK-3β in mood disorder was highlighted by the study of lithium and valproate (Chen et al., *J. Neurochem.*, 1999, 72, 1327-1330; Klein and Melton, *Proc. Natl. Acad. Sci. USA*, 1996, 93, 8455-8459), both of which are GSK-3β inhibitors and are used to treat mood disorders. There are also existing reports from the genetic perspective supporting the role of GSK-3β in the disease physiology of bipolar disorder (Gould, *Expert. Opin. Ther. Targets*, 2006, 10, 377-392).

It was reported a decrease in AKT1 protein levels and its phosphorylation of GSK-3β at Serine-9 in the peripheral lymphocytes and brains of individuals with schizophrenia. Accordingly, this finding supports the proposal that alterations in AKT1-GSK-3β signaling contribute to schizophrenia pathogenesis (Emamian et al., *Nat Genet*, 2004, 36, 131-137).

Additionally, the role of GSK-3β in cancer is a well-accepted phenomenon.

The potential of small molecules that inhibit GSK-3β has been evidenced for some specific cancer treatments (Jia Luo, *Cancer Letters*, 2009, 273, 194-200). GSK-3β expression and activation are associated with prostate cancer progression (Rinnab et al., *Neoplasia*, 2008, 10, 624-633) and the inhibition of GSK3b was also proposed as specific target for pancreatic cancer (Garcea et al., *Current Cancer Drug Targets*, 2007, 7, 209-215) and ovarian cancer (Qi Cao et al., *Cell Research*, 2006, 16 671-677). Acute inhibition of GSK-3β in colon-rectal cancer cells activates p53-dependent apoptosis and antagonizes tumor growth (Ghosh et al., *Clin Cancer Res* 2005, 11, 4580-4588).

The identification of a functional role for GSK-3β in MLL-associated leukaemia suggests that GSK-3β inhibition may be a promising therapy that is selective for transformed cells that are dependent on HOX overexpression (Birch et al., *Cancer Cell*, 2010, 17, 529-531).

GSK-3β is involved in numerous inflammatory signalling pathways, for example, among others GSK-3β inhibition has been shown to induce secretion of the anti-inflammatory cytokine IL-10. According to this finding, GSK-3β inhibitors could be useful to regulate suppression of inflammation (G. Klamer et al., *Current Medicinal Chemistry*, 2010, 17(26), 2873-2281, Wang et al., *Cytokine*, 2010, 53, 130-140).

GSK-3β inhibition has been also shown to attenuate cocaine-induced behaviors in mice. The administration of cocaine in mice pretreated with a GSK-3β inhibitor demonstrated that pharmacological inhibition of GSK3 reduced both the acute behavioral responses to cocaine and the long-term neuroadaptations produced by repeated cocaine (Cocaine-induced hyperactivity and sensitization are dependent on GSK3, Miller J S et al. *Neuropharmacology.* 2009 June; 56(8):1116-23, Epub 2009 Mar. 27).

The role of GSK-3β in the development of several forms of epilepsies has been demonstrated in several studies, which suggest that inhibition of GSK-3β could be a pathway for the treatment of epilepsy (*Novel glycogen synthase kinase 3 and ubiquitination pathways in progressive myoclonus epilepsy*, Lohi H et al., *Hum Mol Genet.* 2005 Sep. 15; 14(18):2727-36 and *Hyperphosphorylation and aggregation of Tau in laforin-deficient mice, an animal model for Lafora disease*, Puri R et al., *J Biol Chem.* 2009 Aug. 21; 284(34):22657-63).

The relationship between GSK-3β inhibition and treatment of pain has been demonstrated by Martins D F et al. in "The antinociceptive effects of AR-A014418, a selective inhibitor of glycogen synthase kinase-3 beta, in mice", J. Pain, 2011 March; 12(3):315-22.

A review on GSK-3β, its function, its therapeutic potential and its possible inhibitors is given in "GSK-3β: role in therapeutic landscape and development of modulators" (S. Phukan et al., *British Journal of Pharmacology* (2010), 160, 1-19).

WO 2004/014864 discloses 1H-indazole-3-carboxamide compounds as selective cyclin-dependant kinases (CDK) inhibitors. Such compounds are assumed to be useful in the treatment of cancer, through a mechanism mediated by $CDK_2$, and neurodegenerative diseases, in particular Alzheimer's disease, through a mechanism mediated by $CDK_5$, and as anti-viral and anti-fungine, through a mechanism mediated by $CDK_7$, $CDK_5$ and $CDK_9$.

Cyclin-dependant kinases (CDKs) are serine/threonine kinases, first discovered for their role in regulating the cell cycle. CDKs are also involved in regulating transcription, mRNA processing, and the differentiation of nerve cells. Such kinases activate only after their interaction and binding with regulatory subunits, namely cyclins.

Moreover, 1H-indazole-3-carboxamide compounds were also described as analgesics in the treatment of chronic and neuropathic pain (see, for example, WO 2004/074275 and WO 2004/101548) and as $5-HT_4$ receptor antagonists, useful in the treatment of gastrointestinal disorders, central nervous system disorders and cardiovascular disorders (see, for example, WO 1994/10174).

SUMMARY OF THE INVENTION

As GSK-3β had been only recently discovered as a pharmacological target, there is a strong need to find compounds that selectively inhibits GSK-3β.

The Applicant has surprisingly found that the 1H-indazole-3-carboxamide compounds of formula (I) are capable of inhibit GSK-3β and have very high affinity for GSK-3β, when compared with other kinases. Thus, said compounds are capable of selectively inhibiting GSK-3β.

Accordingly, the useful compounds according to this invention are capable of selectively inhibiting the activity of GSK-3β and are, therefore, useful for the treatment of the pathological conditions arising from the uncontrolled activation and/or over-expression of GSK-3β, selected from the group comprising (i) insulin-resistance disorders, such as type-2 diabetes, syndrome X, obesity and polycystic ovary syndrome; (ii) neurodegenerative diseases, such as Parkinson's disease, Alzheimer's disease, Huntington's disease and spinal neurodegenerative disorders; (iii) mood disorders, such as bipolar disorders and depressive disorders; (iv) schizophrenic disorders; (v) cancerous disorders, such as prostate, pancreatic, ovarian, and colon-rectal cancer and MLL-associated leukaemia; (vi) inflammation; (vii) substance abuse disorders; and (viii) epilepsies.

Then, in a first aspect, the present invention relates to the use of 1H-indazole-3-carboxamide compounds having the following general formula (I)

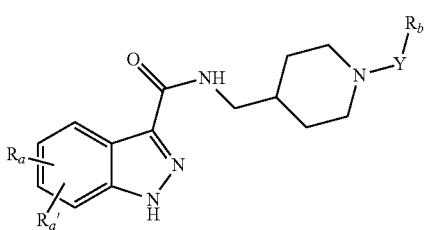

(I)

wherein $R_a$ and $R_a'$, equal or different each other, is a hydrogen atom; a halogen atom; a $C_1$-$C_6$ alkyl, $C_2$-$C_6$ alkenyl, $C_2$-$C_6$ alkynyl and $C_1$-$C_6$ alkoxy group, optionally substituted by one or more substituents selected from the group consisting of halogen, hydroxy, —$NH_2$, and $C_1$-$C_3$ alkoxy; a carbocyclic or heterocyclic ring, aliphatic or aromatic, having from 3 to 12 members, optionally substituted by one or more substituents selected from the group consisting of halogen, hydroxy, $C_1$-$C_6$ alkyl, $C_1$-$C_6$ alkoxy, —C(O)OH, —C(O)OR$_1$ and —C(O)NR$_1$R$_2$;

Y is a bond, a $C_1$-$C_6$ alkyl, $C_2$-$C_6$ alkenyl or $C_2$-$C_6$ alkynyl group, optionally substituted by one or more substituents selected from the group consisting of halogen, hydroxy, —$NH_2$, and $C_1$-$C_3$ alkoxy;

$R_b$ is a carbocyclic or heterocyclic ring, aliphatic or aromatic, having from 3 to 12 members, substituted by one or more substituents selected from the group consisting of halogen, hydroxy, nitro, cyano, —$CF_3$, $C_1$-$C_6$ alkoxy, benzyloxy, $C_1$-$C_4$ alkyl, $C_2$-$C_4$ alkenyl, and $C_2$-$C_4$ alkynyl, —$NHSO_2CH_3$, —$SO_2NH_2$, —Z—C(O)OH, —Z—C(O)OR$_1$ and —Z—C(O)NR$_1$R$_2$, wherein Z is a σ-bond or ($C_1$-$C_3$)alkyl;

$R_1$ and $R_2$ are independently a hydrogen atom, a $C_1$-$C_4$ alkyl group, a $C_2$-$C_4$ alkenyl group, a $C_2$-$C_4$ alkynyl group, and a phenyl group;

and its salts of addition with pharmaceutically acceptable organic and inorganic acids and bases;

for the treatment of a disease arising from the uncontrolled activation and/or over-expression of GSK-3β, selected from the group consisting of (i) insulin-resistance disorders, such as type-2 diabetes, syndrome X, obesity and polycystic ovary syndrome; (ii) neurodegenerative diseases, such as Parkinson's disease, Alzheimer's disease, Huntington's disease and spinal neurodegenerative disorders; (iii) mood disorders, such as bipolar disorders and depressive disorders; (iv) schizophrenic disorders; (v) cancerous disorders, such as prostate, pancreatic, ovarian, and colon-rectal cancer and MLL-associated leukaemia; (vi) inflammation; (vii) substance abuse disorders; and (viii) epilepsies.

In a second aspect, the present invention relates to a method of treatment of a pathological state arising from the uncontrolled activation and/or over-expression of GSK-3β, selected from the group consisting of (i) insulin-resistance disorders, such as type-2 diabetes, syndrome X, obesity and polycystic ovary syndrome; (ii) neurodegenerative diseases, such as Parkinson's disease, Alzheimer's disease, Huntington's disease and spinal neurodegenerative disorders; (iii) mood disorders, such as bipolar disorders and depressive disorders; (iv) schizophrenic disorders; (v) cancerous disorders, such as prostate, pancreatic, ovarian, and colon-rectal cancer and MLL-associated leukaemia; (vi) inflammation; (vii) substance abuse disorders; and (viii) epilepsies by the administration to a human being in need thereof of an effective amount of a 1H-indazole-3-carboxamide having the following general formula (I)

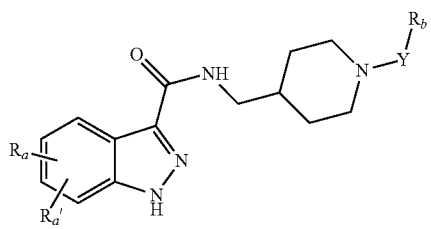

(I)

wherein $R_a$ and $R_a'$, equal or different each other, is a hydrogen atom; a halogen atom; a $C_1$-$C_6$ alkyl, $C_2$-$C_6$ alkenyl, $C_2$-$C_6$ alkynyl and $C_1$-$C_6$ alkoxy group, optionally substituted by one or more substituents selected from the group consisting of halogen, hydroxy, —$NH_2$, and $C_1$-$C_3$ alkoxy; a carbocyclic or heterocyclic ring, aliphatic or aromatic, having from 3 to 12 members, optionally substituted by one or more substituents selected from the group consisting of halogen, hydroxy, $C_1$-$C_6$ alkyl, $C_1$-$C_6$ alkoxy, —NR$_1$R$_2$, —C(O)OH, —C(O)OR$_1$ and —C(O)NR$_1$R$_2$;

Y is a bond, a $C_1$-$C_6$ alkyl, $C_2$-$C_6$ alkenyl or $C_2$-$C_6$ alkynyl group, optionally substituted by one or more substituents selected from the group consisting of halogen, hydroxy, —$NH_2$, and $C_1$-$C_3$ alkoxy;

$R_b$ is a carbocyclic or heterocyclic ring, aliphatic or aromatic, having from 3 to 12 members, substituted by one or more substituents selected from the group consisting of halogen, hydroxy, nitro, cyano, —$CF_3$, $C_1$-$C_6$ alkoxy, benzyloxy, $C_1$-$C_4$ alkyl, $C_2$-$C_4$ alkenyl, and $C_2$-$C_4$ alkynyl, —$NHSO_2CH_3$, —$SO_2NH_2$, —Z—C(O)OH, —Z—C(O)OR$_1$ and —Z—C(O)NR$_1$R$_2$, wherein Z is a σ-bond or ($C_1$-$C_3$)alkyl;

$R_1$ and $R_2$ are independently a hydrogen atom, a $C_1$-$C_4$ alkyl group, a $C_2$-$C_4$ alkenyl group, a $C_2$-$C_4$ alkynyl group, and a phenyl group;

and its salts of addition with pharmaceutically acceptable organic and inorganic acids and bases.

The present invention also includes the prodrugs, stereoisomers, and enantiomers of the compounds of formula (I) described above.

Some compounds falling within the above formula (I) are new, i.e., were never disclosed and exemplified in a printed publication before the date of filing of the present application.

Accordingly, in a third aspect, the present invention relates to 1H-indazole-3-carboxamides compounds of formula:

N-{[1-(2,4-dichlorobenzyl)piperidin-4-yl]methyl}-5-methoxy-1H-indazole-3-carboxamide and N-({1-[4-(benzyloxy)benzyl]piperidin-4-yl}methyl)-5-methoxy-1H-indazole-3-carboxamide.

DETAILED DESCRIPTION OF THE INVENTION

Throughout the present description and the following claims, "$C_{1-6}$ alkyl" is intended to indicate linear or branched alkyl groups having from 1 to 6 carbon atoms, such as methyl, ethyl, propyl, isopropyl, n-butyl, isobutyl, sec-butyl, tert-butyl, n-pentyl, sec-pentyl, 3-pentyl, iso-pentyl, neo-pentyl, n-hexyl, sec-hexyl and neo-hexyl.

Throughout the present description and the following claims, "$C_{1-4}$ alkyl" is intended to indicate linear or branched alkyl groups having from 1 to 4 carbon atoms, such as methyl, ethyl, propyl, isopropyl, n-butyl, isobutyl, sec-butyl and tert-butyl.

Throughout the present description and the following claims, "$C_{1-3}$ alkyl" is intended to indicate linear or branched alkyl groups having from 1 to 3 carbon atoms, such as methyl, ethyl, propyl and isopropyl.

Throughout the present description and the following claims, "$C_{2-6}$ alkenyl" is intended to indicate linear or branched alkyl groups having from 2 to 6 carbon atoms and at least one double bond, such as ethenyl(vinyl), 1-propenyl, 2-propenyl(allyl), isopropenyl, butenyl, pentenyl and hexenyl.

Throughout the present description and the following claims, "$C_{2-4}$ alkenyl" is intended to indicate linear or branched alkyl groups having from 2 to 4 carbon atoms and at least one double bond, such as ethenyl(vinyl), 1-propenyl, 2-propenyl(allyl), isopropenyl and butenyl.

Throughout the present description and the following claims, "$C_{2-6}$ alkynyl" is intended to indicate linear or branched alkyl groups having from 2 to 6 carbon atoms and at least one triple bond, such as ethynyl, 1-propynyl, 2-propynyl(propargyl), butynyl, pentynyl and hexynyl.

Throughout the present description and the following claims, "$C_{2-4}$ alkynyl" is intended to indicate linear or branched alkyl groups having from 2 to 4 carbon atoms and at least one triple bond, such as ethynyl, 1-propynyl, 2-propynyl(propargyl) and butynyl.

Throughout the present description and the following claims, "$C_{1-6}$ alkoxy" is intended to indicate linear or branched alkoxy groups having from 1 to 6 carbon atoms, such as methoxy, ethoxy, n-propoxy, iso-propoxy, n-butoxy, tert-butoxy, n-penthoxy, sec-penthoxy, isopenthoxy and n-esiloxy.

Throughout the present description and the following claims, "$C_{1-3}$ alkoxy" is intended to indicate linear or branched alkoxy groups having from 1 to 3 carbon atoms, such as methoxy, ethoxy, n-propoxy and iso-propoxy.

According to a preferred embodiment of the invention, the meanings of $R_a$, $R_a'$, $R_b$ and Y of the formula (I) above are described here in below.

Preferably, $R_a$ and $R_a'$, equal or different each other, is a hydrogen atom; a halogen atom, selected from chlorine, bromine and iodine; a $C_1$-$C_6$ alkyl, and $C_1$-$C_6$ alkoxy group, optionally substituted by one or more substituents selected from the group consisting of halogen, hydroxy, —$NH_2$, or $C_1$-$C_3$ alkoxy; a carbocyclic or heterocyclic ring, aliphatic or aromatic, having from 4 to 10 members, optionally substituted by one or more substituents selected from the group consisting of halogen, hydroxy, $C_1$-$C_6$ alkyl, $C_1$-$C_6$ alkoxy, —$NR_1R_2$, —C(O)OH, —C(O)$OR_1$ and —C(O)$NR_1R_2$.

More preferably, $R_a$ and $R_a'$, equal or different each other, is a halogen atom, selected from chlorine and bromine; a $C_1$-$C_6$ alkyl group; a $C_1$-$C_6$ alkoxy group; or a carbocyclic or heterocyclic ring, aliphatic or aromatic, having from 5 to 6 members, optionally substituted by one or more substituents, selected from the group consisting of halogen, hydroxy, $C_1$-$C_6$ alkyl, $C_1$-$C_6$ alkoxy, —$NR_1R_2$ and —C(O)OH.

Advantageously, said carbocyclic or heterocyclic ring, aliphatic or aromatic, having 5 or 6 members is selected from phenyl, pyridine, pyrimidine, pyrazine, pyridazine, pyrrole, furan, thiophene, oxazole, isoxazole, thiazole, isothiazole, 2H-pyran, cyclohexyl, cyclopenthyl piperidine, piperazine.

Even more preferably, $R_a$ and $R_a'$, equal or different each other, is a bromine atom, a $C_1$-$C_3$ alkoxy group; or an aromatic carbocyclic or heterocyclic ring, having 6 members, optionally substituted by one or two substituents selected from the group consisting of halogen, hydroxy, $C_1$-$C_3$ alkyl, $C_1$-$C_3$ alkoxy, —$NR_1R_2$ and —C(O)OH.

In a preferred embodiment, said carbocyclic or heterocyclic ring, aliphatic or aromatic, having 6 members is selected from phenyl, pyridine, pyrimidine, pyrazine, pyridazine, 2H-pyran, cyclohexyl, piperidine, piperazine.

In an even more preferred embodiment, said carbocyclic or heterocyclic ring, aliphatic or aromatic, having 6 members is selected from phenyl, pyridine, pyrimidine, 2H-pyran, cyclohexyl.

Preferably, Y is a bond, $C_1$-$C_6$ alkyl group, optionally substituted by one or more substituents selected from the group consisting of halogen, hydroxy, —$NH_2$, and $C_1$-$C_3$ alkoxy.

More preferably, Y is a $C_1$-$C_6$ alkyl group.

Even more preferably, Y is a $C_1$-$C_3$ alkyl group.

Preferably, $R_b$ is a carbocyclic or heterocyclic ring, aliphatic or aromatic, having from 4 to 10 members, substituted by one or more substituents selected from the group consisting of halogen, hydroxy, nitro, cyano, —$CF_3$, $C_1$-$C_6$ alkoxy, benzyloxy, $C_1$-$C_4$ alkyl, —$NHSO_2CH_3$, —$SO_2NH_2$, —Z—C(O)OH, —Z—C(O)$OR_1$ and —Z—C(O)$NR_1R_2$, wherein Z is a σ-bond or ($C_1$-$C_3$)alkyl.

More preferably, $R_b$ is a carbocyclic or heterocyclic ring, aliphatic or aromatic, having from 5 to 6 members, substituted by one or more substituents, selected from the group consisting of halogen, hydroxy, nitro, —$CF_3$, $C_1$-$C_6$ alkoxy, benzyloxy, —$NHSO_2CH_3$, —$SO_2NH_2$, —Z—C(O)OH and —Z—C(O)$OR_1$, wherein Z is a σ-bond or ($C_1$-$C_3$)alkyl.

Advantageously, said carbocyclic or heterocyclic ring, aliphatic or aromatic, having 5 or 6 members is selected from phenyl, pyridine, pyrimidine, pyrazine, pyridazine, morpholine, pyrrole, furan, thiophene, oxazole, isoxazole, thiazole, isothiazole, 1-oxa-2,4-diazole, 2H-pyran, cyclohexyl, cyclopenthyl piperidine, piperazine.

Even more preferably, $R_b$ is an aromatic carbocyclic ring having 6 members substituted by one or two substituents selected from the group consisting of halogen, hydroxy, nitro, —$CF_3$, $C_1$-$C_3$ alkoxy and benzyloxy.

In a preferred embodiment, said carbocyclic or heterocyclic ring, aliphatic or aromatic, having 6 members is selected from phenyl, pyridine, pyrimidine, pyrazine, pyridazine, morpholine, 2H-pyran, cyclohexyl, piperidine, piperazine.

In an even more preferred embodiment, said carbocyclic or heterocyclic ring, aliphatic or aromatic, having 6 members is selected from phenyl, pyridine, pyrimidine, morpholine, 2H-pyran, cyclohexyl.

In an even more preferred embodiment, said carbocyclic or heterocyclic ring, aliphatic or aromatic, having 5 members is selected from furan, thiophene, thiazole, oxazole, and 1-oxa-2,4-diazole.

Preferably, $R_1$ and $R_2$ are independently a hydrogen atom, a $C_1$-$C_4$ alkyl group, or a phenyl group.

More preferably, $R_1$ and $R_2$ are independently a $C_1$-$C_3$ alkyl group.

Even more preferably, $R_1$ and $R_2$ are both a methyl group.

Preferably, said carbocyclic or eterocyclic ring, aliphatic or aromatic, having from 5 to 6 members is selected from the group consisting of phenyl, ciclohexane, ciclopentane, pyridine, pyrazine, pyrimidine, pyridazine, piperidine, piperazine, furan, thiophene, pyrrole, pyrrolidine, imidazole, morpholine, thiazole, thiazolidine, thiadiazole, thiadiazolidine, oxazole, oxazolidine, isoxazole, isoxazolidine, pyrazole.

More preferably, said carbocyclic ring is phenyl and said etherocyclic ring is pyridine, oxazole, imidazole and pyrrole.

The compounds useful in the present invention are preferably employed as salts with pharmaceutically acceptable organic and inorganic acids or bases.

Preferably, the pharmaceutically acceptable organic acids are selected from the group consisting of oxalic, maleic, methanesuiphonic, paratoluenesulphonic, succinic, citric, malic, tartaric lactic acid.

Preferably, the pharmaceutically acceptable organic bases are selected from the group consisting of tromethamine, lysine, arginine, glycine, alanine and ethanolamine.

Preferably, the pharmaceutically acceptable inorganic acids are selected from the group consisting of hydrochloric, hydrobromic, phosphoric and sulfuric acid.

Preferably, the pharmaceutically acceptable inorganic bases are selected from the group consisting of hydroxide or carbonate of alkaline or alkaline-earth metals, such as sodium, potassium and calcium.

The present invention also includes the use of prodrugs, stereoisomers, and enantiomers of the compounds of formula (I) described above.

As used herein the term "prodrug" refers to an agent, which is converted into the parent drug in vivo by some physiological chemical process (e.g., a prodrug on being brought to the physiological pH is converted to the desired drug form). Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a prodrug would be a compound of the present invention wherein it is administered as an ester (the "prodrug") to facilitate transmittal across a cell membrane where water solubility is not beneficial, but then it is metabolically hydrolyzed to the carboxylic acid once inside the cell where water solubility is beneficial.

Prodrugs have many useful properties. For example, a prodrug may be more water-soluble than the ultimate drug, thereby facilitating intravenous administration of the drug. A prodrug may also have a higher level of oral bioavailability than the ultimate drug. After administration, the prodrug is enzymatically or chemically cleaved to deliver the ultimate drug in the blood or tissue.

Ester prodrugs of the compounds disclosed herein are specifically contemplated. An ester may be formed from a carboxylic acid functional group linked to a compound of formula (I) above by reaction with an alcohol or phenol. Alternatively, an ester may be formed from a hydroxyl functional group linked to a compound of formula (I) above by reaction with a carboxylic acid or an aminoacid. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$alkyl esters are particularly useful, where alkyl part of the ester has from 1 to 6 carbon atoms and includes, but is not limited to, methyl, ethyl, propyl, isopropyl, n-butyl, sec-butyl, isobutyl, t-butyl, pentyl isomers, hexyl isomers, cyclopropyl, cyclobutyl, cyclopentyl, cyclohexyl, and combinations thereof having from 1-6 carbon atoms.

The compounds of the present invention according to formula (I) above can be used for the treatment of a pathological state arising from the uncontrolled activation and/or overexpression of GSK-3β, selected from the group consisting of (i) insulin-resistance disorders; (ii) neurodegenerative diseases; (iii) mood disorders; (iv) schizophrenic disorders; (v) cancerous disorders; (vi) inflammation; (vii) substance abuse disorders; and (viii) epilepsies.

Advantageously, insulin-resistance disorders are type-2 diabetes, syndrome X, obesity and polycystic ovary syndrome.

Advantageously, acute and chronic neurodegenerative diseases are Parkinson's disease, Alzheimer's disease, Huntington's disease and spinal neurodegenerative disorders.

Preferably, spinal neurodegenerative disorders are amyotrophic lateral sclerosis, multiple sclerosis, spinal muscular atrophy and neurodegeneration due to spinal cord injury.

Advantageously, mood disorders are bipolar disorders and depressive disorders.

Preferably, bipolar disorders are bipolar I, bipolar II, cyclothymia and bipolar disorder not otherwise specified (BD-NOS), Preferably, depressive disorders are major depressive disorder (MDD), atypical depression (AD), melancholic depression, psychotic major depression (PMD), catatonic depression, postpartum depression (PPD), seasonal affective disorder (SAD), dysthymia, and depressive disorder not otherwise specified (DD-NOS)

Advantageously, schizophrenic disorders are paranoid schizophrenia, disorganized schizophrenia, catatonic schizophrenia, simple schizophrenia, residual schizophrenia, and undifferentiated schizophrenia.

Advantageously, cancerous disorders are prostate, pancreatic, ovarian, and colon-rectal cancer and MLL-associated leukaemia.

Advantageously, substance abuse disorders are abuse disorders due to psychostimulants.

Typically, the 1H-indazole-3-carboxamide according to formula (I) useful in this invention are administered in the form of a pharmaceutical composition.

Accordingly, a further aspect of the present invention relates to a pharmaceutical composition comprising at least one compound of formula (I) as described above and at least one inert pharmaceutically acceptable excipient, for use in the treatment of a pathological state arising from the uncontrolled activation and/or over-expression of GSK-3β, selected from the group consisting of (i) insulin-resistance disorders, such as type-2 diabetes, syndrome X, obesity and polycystic ovary syndrome; (ii) neurodegenerative diseases, such as Parkinson's disease, Alzheimer's disease, Huntington's disease, and spinal neurodegenerative disorders; (iii) mood disorders, such as bipolar disorders and depressive disorders; (iv) schizophrenic disorders; (v) cancerous disorders, such as prostate, pancreatic, ovarian, and colon-rectal cancer and MLL-associated leukaemia; (vi) inflammation, (vii) substance abuse disorders; and (viii) epilepsies.

Preferably, the pharmaceutical composition of the present invention is prepared in suitable dosage forms comprising an effective amount of at least one compound of formula (I) as described above, a salt thereof with a pharmaceutically acceptable organic or inorganic acid or base, or a prodrug thereof, and at least one inert pharmaceutically acceptable excipient.

Examples of suitable dosage forms are tablets, capsules, coated tablets, granules, solutions and syrups for oral administration; solutions, pomade and ointment for topical administration; medicated patches for transdermal administration; suppositories for rectal administration and injectable sterile solutions.

Other suitable dosage forms are those with sustained release and those based on liposomes for oral, injectable or transdermal administration.

The dosage forms can also contain other traditional ingredients such as: preservatives, stabilizers, surfactants, buffers, salts for regulating osmotic pressure, emulsifiers, sweeteners, colorants, flavourings and the like.

The amount of the 1H-indazole-3-carboxamide according to formula (I) or of the pharmaceutically acceptable salt of acid addition thereof in the pharmaceutical composition of the present invention can vary over a wide range depending on known factors, for example, the type of pathology, the severity of the disease, the patient's body weight, the dosage form, the chosen route of administration, the number of administrations per day and the efficacy of the selected 1H-indazole-3-carboxamide compound according to formula (I). However, a person skilled in the art can determine the optimum amount in easily and routinely manner.

Typically, the amount of compound of formula (I) or of the pharmaceutically acceptable salt of acid addition thereof in the pharmaceutical composition of the present invention will be such as to ensure a level of administration from 0.0001 to 100 mg/kg/day. Preferably, the level of administration is from 0.001 to 50 mg/kg/day, and even more preferably from 0.01 to 10 mg/kg/day.

The dosage forms of the pharmaceutical composition of the present invention can be prepared by techniques that are familiar to a pharmaceutical chemist, and comprise mixing, granulation, compression, dissolution, sterilization and the like.

Non-limiting examples of compounds of formula (I) that are useful according to the present invention are those of the following table 1.

TABLE 1

| | IUPAC name | Structure |
|---|---|---|
| 1 | N-({1-[2-(4-hydroxyphenyl)ethyl]-piperidin-4-yl}methyl)-5-methoxy-1H-indazole-3-carboxamide | 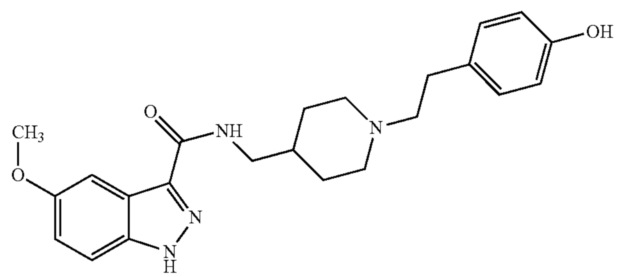 [SMILES: COc1ccc2[nH]nc(C(=O)NCC3CCN(CCc4ccc(O)cc4)CC3)c2c1] |
| 2 | 5-methoxy-N-({1-[2-(4-methoxyphenyl)ethyl]piperidin-4-yl}methyl)-1H-indazole-3-carboxamide | 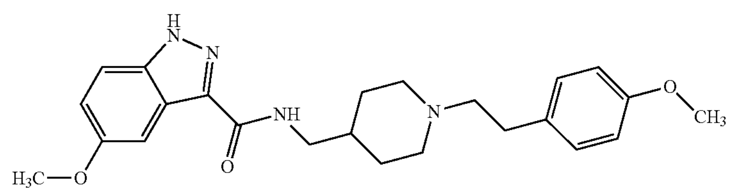 |
| 3 | N-{[1-(2,4-dichlorobenzyl)piperidin-4-yl]methyl}-5-methoxy-1H-indazole-3-carboxamide | 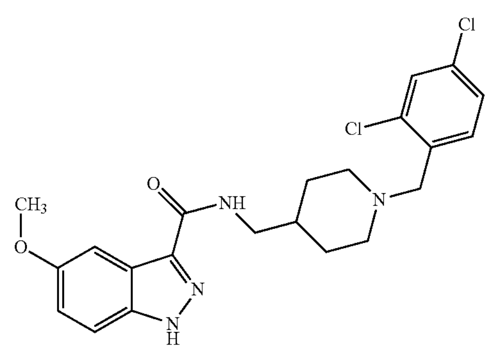 [SMILES: COc1ccc2[nH]nc(C(=O)NCC3CCN(Cc4ccc(Cl)cc4Cl)CC3)c2c1] |
| 4 | 5-methoxy-N-({1-[4-(trifluoromethyl)benzyl]piperidin-4-yl}methyl)-1H-indazole-3-carboxamide | 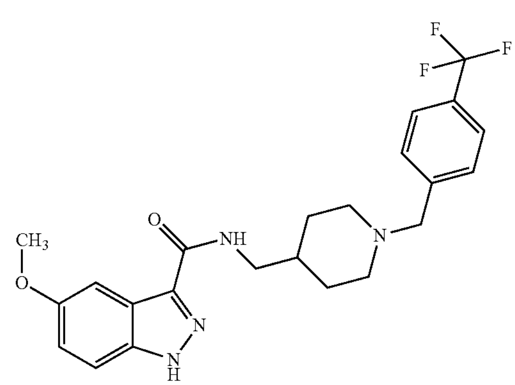 [SMILES: COc1ccc2[nH]nc(C(=O)NCC3CCN(Cc4ccc(C(F)(F)F)cc4)CC3)c2c1] |

TABLE 1-continued

| | IUPAC name | Structure |
|---|---|---|
| 5 | N-({1-[4-(benzyloxy)benzyl]piperidin-4-yl}methyl)-5-methoxy-1H-indazole-3-carboxamide | 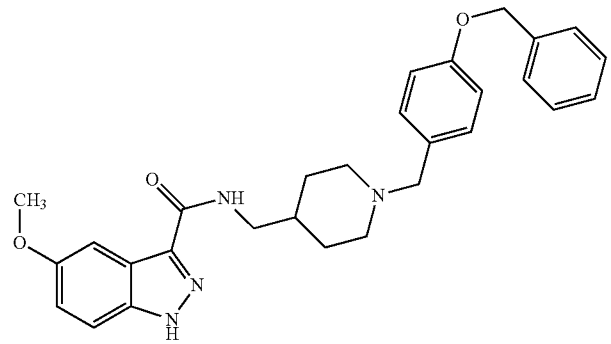 [SMILES: COc1ccc2[nH]nc(C(=O)NCC3CCN(Cc4ccc(OCc5ccccc5)cc4)CC3)c2c1] |
| 6 | N-{[1-(4-hydroxybenzyl)piperidin-4-yl]methyl}-5-methoxy-1H-indazole-3-carboxamide | 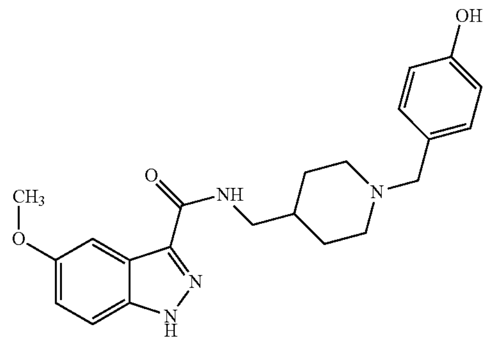 [SMILES: COc1ccc2[nH]nc(C(=O)NCC3CCN(Cc4ccc(O)cc4)CC3)c2c1] |

EXPERIMENTAL PART $^1$H-NMR spectroscopy: internal standard=Tetramethylsilane; DMSO-d$_6$=deuterated dimethyl sulfoxide; (s)=singlet; (d)=doublet; (t)=triplet; (br)=broad; (dd)=double doublet; (dt)=double triplet; (ddd)=double double doublet; (dtd)=double triple doublet; (m)=multiplet; J=coupling constant; δ=chemical shift (in ppm).

Preparation of Compounds of Formula (I)

Compounds of formula (I) can be obtained by methods known to persons skilled in the art, for example by the following methods A to D.

Method A

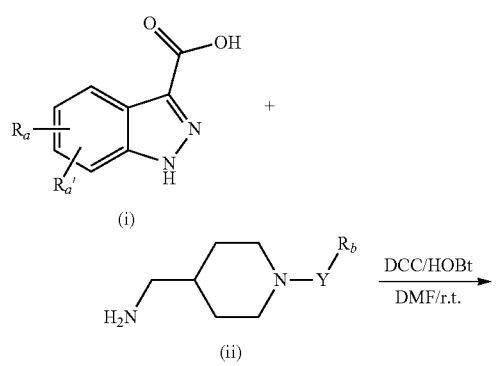

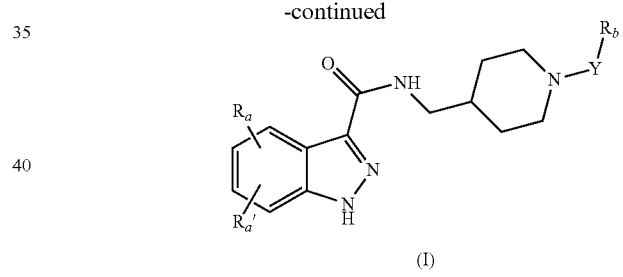

1-Hydroxybenzotriazole (HOBt, 7.40 g, 54.8 mmoles) and N,N'-dicyclohexylcarbodiimide (DCC, 11 g, 53.3 mmoles) were added to a solution of a convenient substituted 1H-indazole-3-carboxylic acid (compound i, 12 g, 49.8 mmoles) in DMF (200 ml) at 0° C. After 1 hour, a solution of a convenient 1-substituted [piperidin-4-yl]methanamine (compound ii, 10 g, 58.1 mmoles) in DMF (100 ml) was added at the same temperature. The mixture was stirred at 0° C. for 2 hours then it was left to reach room temperature during the night. The mixture was diluted with AcOEt then the solid was removed by filtration. The solution was extracted three time with hydrochloridric acid (HCl) 2N. The pH of the acid phase was increased (about 13) with 5N NaOH and solution was extracted three times with dichloromethane (DCM). The organic phase was dried with anhydrous Na$_2$SO$_4$.

The solvent was filtered, evaporated under reduced pressure and the residue was adequately purified.

The following intermediate compounds (a-d) can be used as compound (ii) in the synthetic pathway above:

a) 1-{1-[2-(4-methoxyphenyl)ethyl]piperidin-4-yl}-methanamine

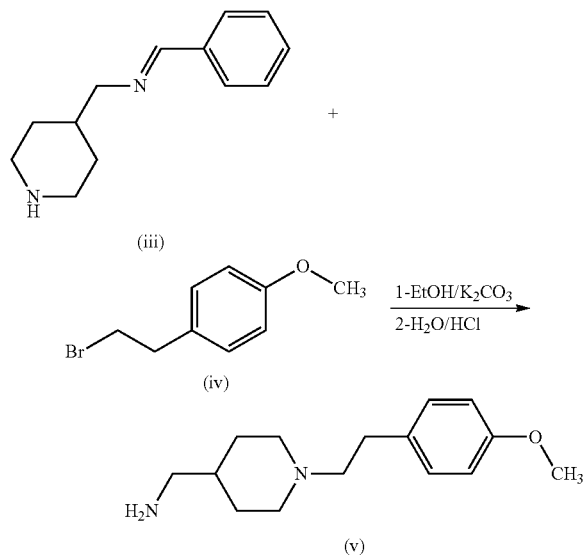

To a stirred solution of N-[phenylmethylidene]-1-(piperidin-4-yl)methanamine (compound iii; 0.158 moles; 31.9 g), prepared as described in WO2004/101548 in absolute ethanol (70 ml), 1-(2-bromoethyl)-4-methoxybenzene (compound iv; 0.237 moles; 32.7 g) and potassium carbonate were added.

The solution was refluxed for 8 hours, then cooled and concentrated by evaporating the solvent under reduced pressure. The reaction mixture was diluted with 3N HCl and stirred at room temperature for 3 hours. The acid solution was then washed with dichloromethane and made alkaline. The aqueous phase was extracted with three portions of dichloromethane, which were reunited and dried over $Na_2SO_4$.

The solvent was removed by evaporating under reduced pressure and the product (v) thus obtained was used as such without any further purification.

$^1$H NMR (300 MHz, DMSO-$d_6$). δ 7.00-7.19 (m, 2H), 6.76-6.89 (m, 2H), 3.71 (s, 3H), 2.91 (d, J=11.56 Hz, 2H), 2.55-2.72 (m, 4H), 2.37-2.47 (m, 2H), 1.90 (dt, J=1.98, 11.56 Hz, 2H), 1.70 (d, J=11.89 Hz, 2H), 1.52 (ddd, J=3.96, 7.27, 10.90 Hz, 1H), 1.15 (dtd, J=3.80, 12.01, 12.14 Hz, 2H).

[M.M.+H$^+$] calculated 249.1961; [M.M.+H$^+$] found 249.1950 b) 1-[1-(2,4-dichlorobenzyl)piperidin-4-yl]methanamine

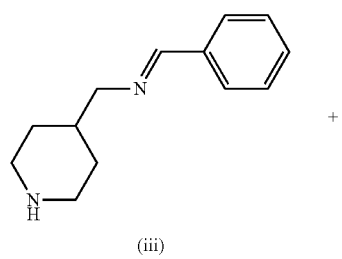

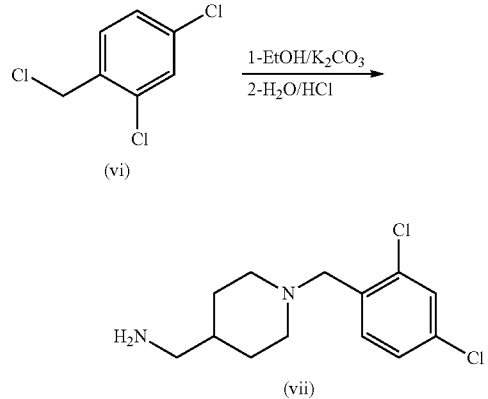

The intermediate (vii) has been prepared by means of the same method described for the preparation of intermediate (v), using 2,4-dichloro-1-(chloromethyl)benzene (compound vi) as starting reagent.

The product (vii) has been purified with flash chromatography (SiO$_2$, CHCl$_3$/MeOH=9/1).

c) 1-{1-[4-(trifluoromethyl)benzyl]piperidin-4-yl}methanamine

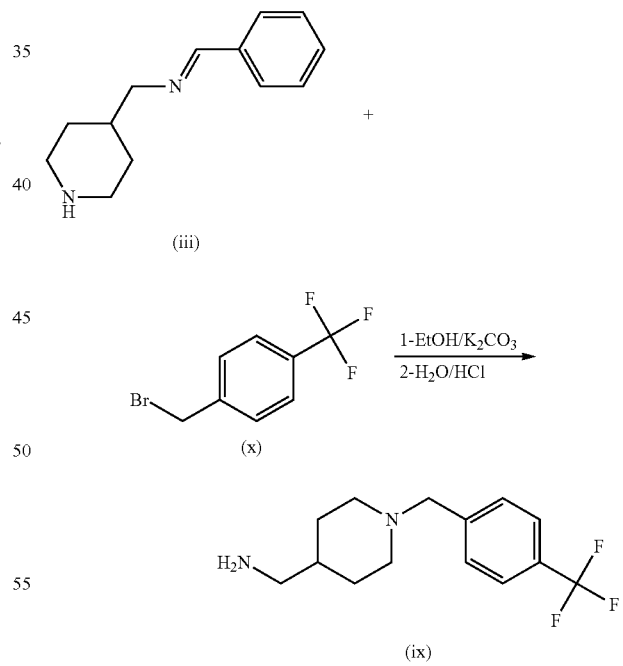

The intermediate (ix) has been prepared by means of the same method described for the preparation of intermediate (v), using 1-(bromomethyl)-4-(trifluoromethyl)benzene (compound viii) as starting reagent.

The product (ix) has been purified with flash chromatography (SiO$_2$, CHCl$_3$/MeOH=9/1).

d) 1-{1-[4-(benzyloxy)benzyl]piperidin-4-yl}methanamine

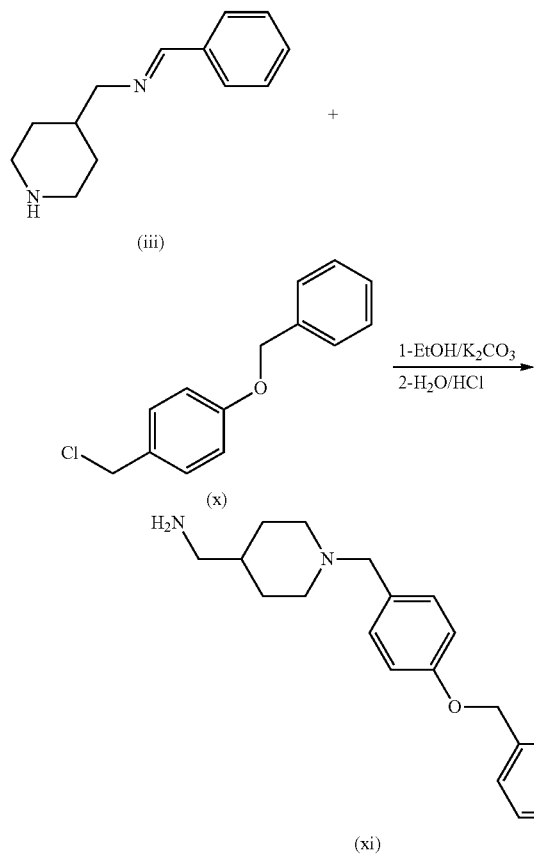

The intermediate (xi) has been prepared by means of the same method described for the preparation of intermediate (v), using 1-(benzyloxy)-4-(chloromethyl)benzene (compound x) as starting reagent.

The product (xi) thus obtained was used as such without any further purification.

For example, compounds (5) and (6) can be prepared according to method A as described below.

Compound (5):

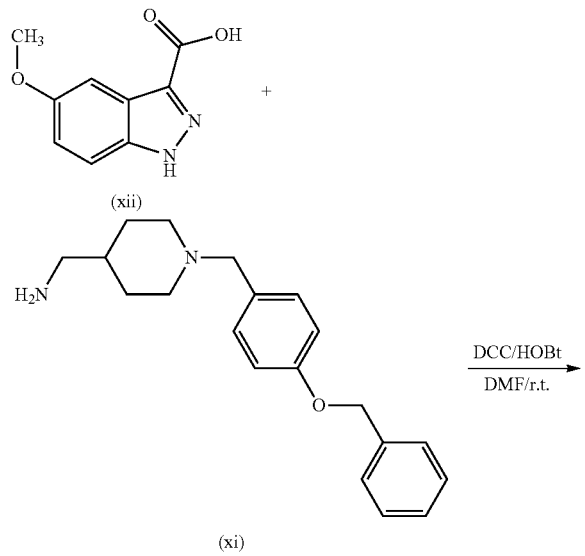

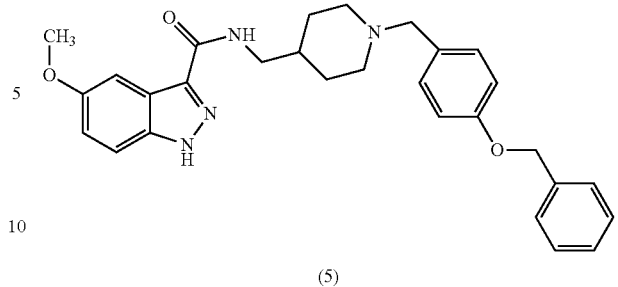

Compound (5) can be prepared using compounds (xii) and (xi) as starting materials, following method A disclosed above.

Compound (6):

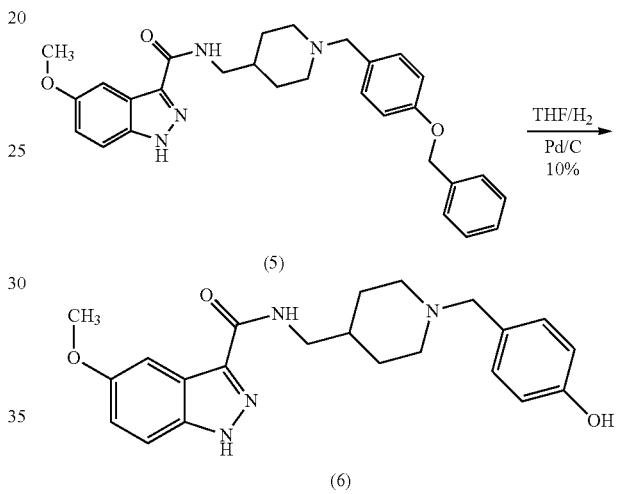

Compound (5) (0.6 mmoles) was hydrogenated in a micro reactor continuous flow system (H-Cube) using CartCart Pd/C 10% as cartridge. Key parameters of H-Cube were set as follows: temperature 80° C.; pressure 1 bar; flow 1 ml/minute.

The solvent was removed by evaporating under reduced pressure, and the compound (6) was purified as disclosed in Table 2.

Method B

First Step:

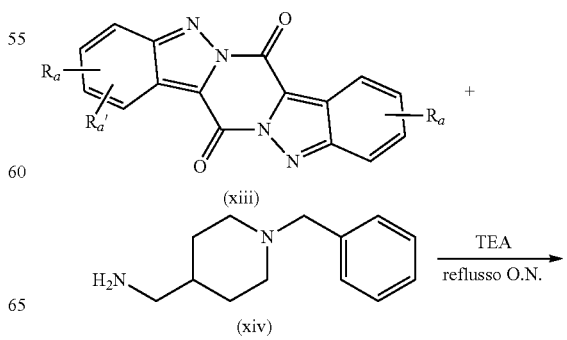

-continued

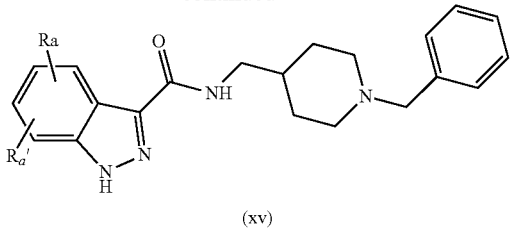

(xv)

To a suspension of a convenient compound (xiii) (2.13 g; 0.0061 moles) in toluene (50 ml) was added drop wise a solution of 1-(1-benzylpiperidin-4-yl)methanamine (compound xiv; 2.52 g; 0.012 moles), prepared as described in WO 94/10174, and triethylamine (TEA; 3.2 ml; 0.023 moles) in toluene (10 ml). The reaction mixture was refluxed for 12 hours, and then filtered. Solvent was removed by evaporation under reduced pressure and residue was taken up with ethyl acetate. The organic phase was transferred into a separated funnel, washed with saturated NaHCO$_3$ solution and water, separated out and dried over Na$_2$SO$_4$.

The product obtained (xv) was adequately crystallized.

Second Step:

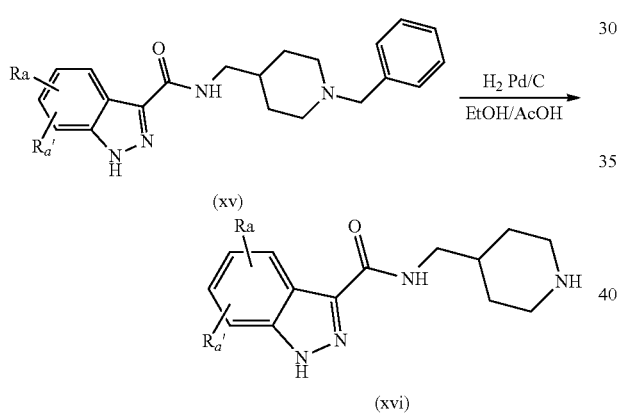

A solution of a convenient N-[(1-benzylpiperidin-4-yl)methyl]-1H-indazole-3-carboxamide (compound xv; 0.506 g; 1.34 mmol) in absolute ethanol (8 ml) and glacial acetic acid (0.8 ml) was hydrogenated in a micro reactor continuous flow system (H-Cube) using CartCart Pd/C 10% as cartridge. Key parameters of H-Cube were set as follow: temperature 80°; pressure 10 bar; flow 1 ml/minute.

After three hours, the solution was concentrated by reduced pressure, diluted with water and transferred into a separating funnel. The aqueous phase was then washed with ethyl acetate, made alkaline with 1N NaOH and extracted with ethyl acetate. The organic layers were collected, dried over Na$_2$SO$_4$ and solvent was removed by evaporation under reduced pressure.

The solid thus obtained was dried in a stove under vacuum to give 0.27 g of the desired substituted N-(piperidin-4-ylmethyl)-1H-indazole-3-carboxamide (xvi), which was used without any further purification.

Third Step:

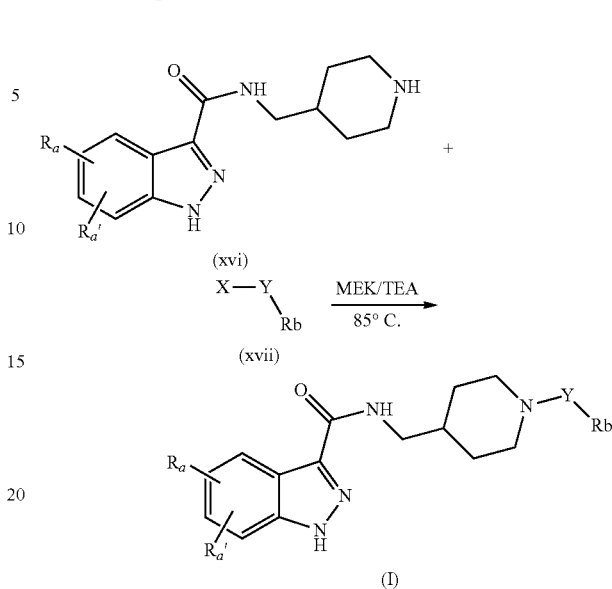

To a solution of compound (xvi) (0.75 mmol; 215 mg) in methyl-ethyl-ketone (MEK; 9 ml) stirred at 85° C., the convenient halogenated compound (xvii; 1.05 Eq) and triethylamine (TEA; 210 µl; 2 Eq) were added drop wise. The reaction mixture was refluxed for 8 hours, then cooled and diluted with ethyl acetate. The organic layer was washed with a saturated NH$_4$Cl solution and water. The organic phase was separated out and dried over Na$_2$SO$_4$.

The solvent was removed by evaporating under reduced pressure, and the product (I) was purified as described in Table 2.

Method C

First Step:

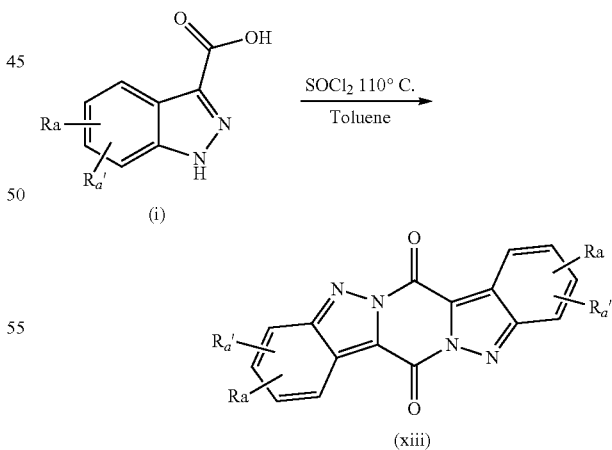

Thionyl chloride (SOCl$_2$; 9.3 ml; 0.128 moles) was added to a suspension of a convenient substituted 1H-indazole-3-carboxylic acid (compound i; 2.36 g; 0.0123 moles) in toluene (77 ml), and the reaction mixture was refluxed for 4 hours. The solvent was removed by evaporation under reduced pressure and the residue was taken up twice in toluene to give 2.13 g of the desired product (xiii) 2,10-substituted 7H,14H-pyrazino[1,2-b:4,5-b']di-indazole-7,14-dione.

Second Step:

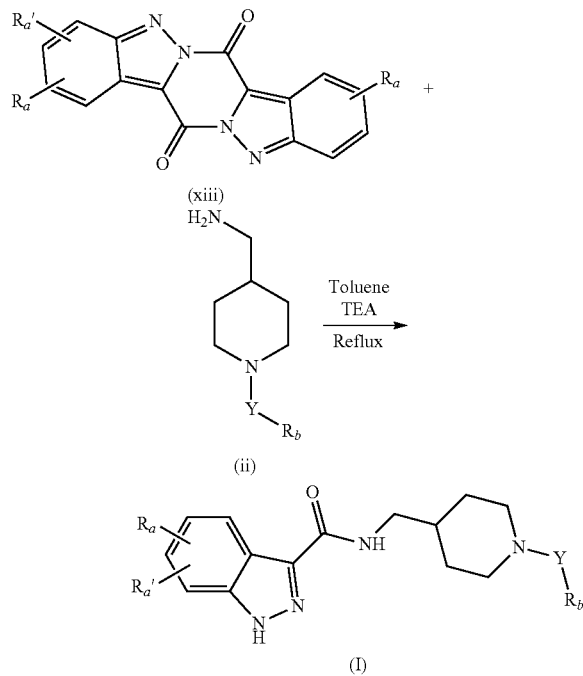

To a suspension of (xiii) (5.2 mmol) in toluene (40 ml), a solution of the convenient amine (compound ii; 2, 1 Eq) and triethylamine (TEA; 3, 6 Eq; 2.6 ml) was added drop wise. The mixture reaction was refluxed for 8 hours, then cooled and stirred in 2N HCl (20 ml) for 8 hours. The suspension was transferred in a separating funnel and aqueous phase was separating out and made alkaline with 1N NaOH.

The solvent was removed by evaporating under reduced pressure, and the product (I) was purified as described below.

For example, compound (3) can be prepared following method C described below.

Compound (3):

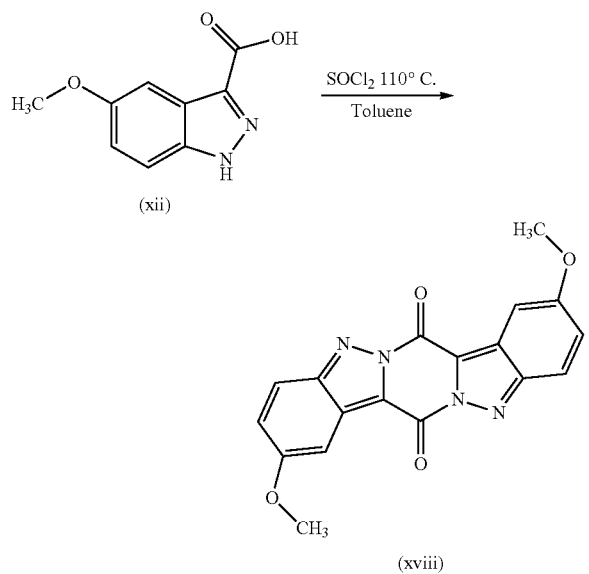

Thionyl chloride (SOCl$_2$; 9.3 ml; 0.128 moles) was added to a suspension of 5-methoxy-1H-indazole-3-carboxylic acid (compound xii; 2.36 g; 0.0123 moles) in toluene (77 ml), and the reaction mixture was refluxed for 4 hours. The solvent was removed by evaporation under reduced pressure and the residue was taken up twice in toluene to give 2.13 g of the desired product 2,10-dimethoxy-7H,14H-pyrazino[1,2-b:4,5-b']di-indazole-7,14-dione (xviii).

$^1$H NMR (300 MHz, CHLOROFORM-d): δ 8.53 (dd, J=0.58, 9.17 Hz, 2H), 7.64 (d, J=1.98 Hz, 2H), 7.35 (dd, J=2.48, 9.08 Hz, 2H), 3.97 (s, 6H).

[M.M.+H$^+$] calculated 349.0937; [M.M.+H$^+$] found 349.0922.

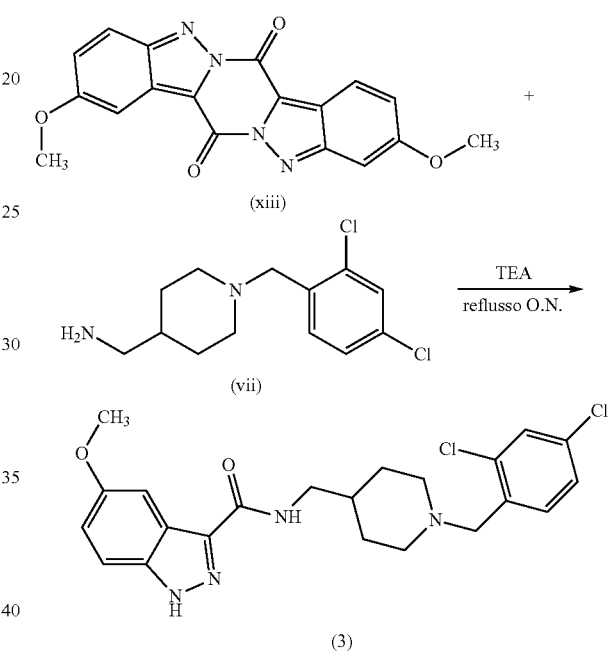

To a suspension of compound (xviii) (2.13 g; 0.0061 moles) in toluene (50 ml) was added drop wise a solution of the intermediate compound (vii) (2.52 g; 0.012 moles), prepared as described in method A, and triethylamine (TEA; 3.2 ml; 0.023 moles) in toluene (10 ml). The reaction mixture was refluxed for 12 hours, and then filtered. Solvent was removed by evaporation under reduced pressure and residue was taken up with ethyl acetate. The organic phase was transferred into a separated funnel, washed with saturated NaHCO$_3$ solution and water, separated out and dried over Na$_2$SO$_4$.

Compound (3) thus obtained was crystallized as disclosed in following Table 2.

$^1$H NMR (300 MHz, DMSO-d$_6$): δ 13.39 (br. s., 1H), 8.25 (t, J=6.04 Hz, 1H), 7.56 (d, J=2.01 Hz, 1H), 7.50 (dd, J=0.55, 8.96 Hz, 1H), 7.17-7.36 (m, 5H), 7.05 (dd, J=2.47, 9.06 Hz, 1H), 3.80 (s, 3H), 3.43 (s, 2H), 3.20 (t, J=6.13 Hz, 2H), 2.79 (d, J=11.16 Hz, 2H), 1.89 (t, J=10.61 Hz, 2H), 1.46-1.74 (m, 3H), 1.07-1.34 (m, 2H).

[M.M.+H$^+$] calculated 379.2134; [M.M.+H$^+$] found 379.2129

Method D

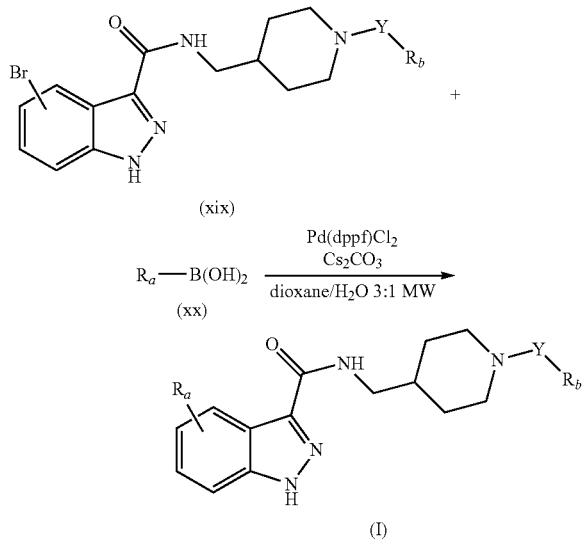

A solution of product (xix), a conveniently substituted arylboronic acid (compound xx), [1,1'-bis(diphenylphosphino)ferrocene]-dichloro-palladium(II) [Pd(dppf)Cl$_2$], caesium carbonate in 1,4-dioxane and water (ratio 3:1) was subjected to microwave irradiation.

Programme was set as follows:

3'; T$_1$=160° C., T$_2$=130° C.; max power 300 W
45'; T$_1$=160° C., T$_2$=130° C.; max power 300 W
5'; T$_1$=20° C., T$_2$=15° C.

After one cycle of microwave irradiation, solvents were removed by evaporating under reduce pressure and the reaction mixture was diluted with a solution of chloroform and methanol in a 2:1 ratio and filtered.

Products (I) thus obtained were purified as described below.

Purification Methods

Compounds of formula (I), obtained according to one of method A to D, can be purified with one of the following techniques (a)-(c).

(a) Flash Chromatography on Silica Gel.

Flash chromatography was carried out with a Biotage Flash Master Personal system on 20-45 µM silica cartridge or Grace Reveleris flash chromatography system with 40 µM silica cartridge.

Flow=60 ml/min.

The solvents used as eluents are shown in the following Table 2.

(b) Crystallization

A different crystallization solvent was used depending on the compound to be purified. The solvents are shown in the following Table 2.

(c) Preparative LC/MS System.

LC/MS system consisted of a Waters 2767 Sample manager, a Waters 2478 dual λ, absorbance detector and a Waters Micromass ZQ single quadrupole mass spectrometer with an electrospray ionization (ESI) source. The column used was a X-Bridge Prep C18 5 µm with 19×10 mm (Waters) pre-column. Fraction collection was available from the system software MassLynx™ v. 4.1. Detection wavelength was set to 230 nm and temperature to 25° C.

The sample was dissolved (50 mg/ml) in DMSO/CH$_3$CN in 1:1 ratio. The mobile phase was:

channel A=CH$_3$CN+0.1% formic acid (Eluent A)
channel B=H$_2$O+0.1% formic acid (Eluent B)
flow=40 ml/min gradient=minimum and maximum percentage of eluent A reached in 15 minutes ranges from 2 to 20 and from 25 to 55, respectively.

The following Table 2 shows both the preparation and the purification method for each compound of formula (I), as listed in Table 1, and the monoisotopic mass for each compound.

TABLE 2

| N° | Preparation method | Purification method | Parameters or solvent used for the purification | MM founded [M + H⁺] | MM calculated [M + H⁺] |
|---|---|---|---|---|---|
| 1 | B | (b) | CHCl$_3$ | 409.2226 | 409.2234 |
| 2 | C | (b) | EtOH abs/AcOEt | 423.2402 | 423.2396 |
| 3 | C | (b) | Hex/AcOEt | 447.1357 | 447.1349 |
| 4 | C | (a) | CHCl$_3$/MeOH | 447.2003 | 447.2002 |
| 5 | A or C | (b) | THF | 485.2548 | 485.2547 |
| 6 | A | (a) | CHCl$_3$/MeOH | 395.2083 | 395.2078 |

MM: monoisotopic mass
CHCl$_3$: chloroform
EtOH abs: absolute ethanol
AcOEt: ethyl acetate
Hex: hexane
MeOH: methanol
THF: tetrahydrofurane

TABLE 3

| N° | 1H-NMR peaks |
|---|---|
| 1 | DMSO-d6; δ 13.40 (br. S., 1H), 9.07 (s, 1H), 8.26 (t, J = 6.16 Hz, 1H), 7.55 (d, J = 2.42 Hz, 1H), 7.50 (dd, J = 0.61, 9.08 Hz, 1H), 7.05 (dd, J = 2.50, 9.10 Hz, 1H), 6.94-7.02 (m, 2H), 6.60-6.68 (m, 2H), 3.80 (s, 3H), 3.19 (t, J = 6.36 Hz, 2H), 2.89 (d, J = 11.30 Hz, 2H), 2.53-2.65 (m, 2H), 2.30-2.46 (m, 2H), 1.79-2.00 (m, 2H), 1.47-1.74 (m, 3H), 1.06-1.31 (m, 2H) |
| 2 | DMSO-d6; δ 13.62 (br. s., 1H), 8.24 (t, J = 6.06 Hz, 1H), 7.55 (d, J = 2.42 Hz, 1H), 7.52 (dd, J = 0.61, 8.88 Hz, 1H), 7.07-7.16 (m, 2H), 7.03 (dd, J = 2.42, 8.88 Hz, 1H), 6.75-6.87 (m, 2H), 3.80 (s, 3H), 3.71 (s, 3H), 3.19 (t, J = 6.26 Hz, 2H), 2.90 (d, J = 11.10 Hz, 2H), 2.57-2.74 (m, 2H), 2.34-2.47 (m, 2H), 1.80-1.98 (m, 2H), 1.46-1.76 (m, 3H), 1.08-1.30 (m, 2H) |
| 3 | DMSO-d6; δ 13.38 (br. s., 1H), 8.28 (t, J = 6.22 Hz, 1H), 7.56 (t, J = 2.38 Hz, 2H), 7.52 (d, J = 2.56 Hz, 1H), 7.50 (d, J = 1.83 Hz, 1H), 7.41 (dd, J = 2.20, 8.20 Hz, 1H), 7.06 (dd, J = 2.56, 9.15 Hz, 1H), 3.81 (s, 3H), 3.51 (s, 2H), 3.21 (t, J = 6.22 Hz, 2H), 2.80 (d, J = 11.34 Hz, 2H), 2.01 (t, J = 10.79 Hz, 2H), 1.48-1.78 (m, 3H), 1.07-1.35 (m, 2H) |
| 4 | DMSO-d$_6$; δ 13.40 (s, 1H), 8.27 (t, J = 6.10 Hz, 1H), 7.67 (d, J = 8.01 Hz, 2H), 7.47-7.57 (m, 4H), 7.05 (dd, J = 2.44, 9.06 Hz, 1H), 3.80 (s, 3H), 3.53 (s, 2H), 3.20 (t, J = 6.27 Hz, 2H), 2.78 (d, J = 11.50 Hz, 2H), 1.94 (t, J = 10.80 Hz, 2H), 1.47-1.77 (m, 3H), 1.12-1.36 (m, 2H) |
| 5 | DMSO-d$_6$; δ 13.44 (br. s., 1H), 8.25 (t, J = 6.22 Hz, 1H), 7.55 (d, J = 1.83 Hz, 1H), 7.50 (d, J = 9.15 Hz, 1H), 7.28-7.46 (m, 5H), 7.14-7.21 (m, 2H), 7.04 (dd, J = 2.38, 8.96 Hz, 1H), 6.88-6.98 (m, 2H), 5.07 (s, 2H), 3.79 (s, 3H), 3.35 (s, 2H), 3.18 (t, J = 6.22 Hz, 2H), 2.77 (d, J = 11.34 Hz, 2H), 1.85 (t, J = 10.79 Hz, 2H), 1.45-1.72 (m, 3H), 1.00-1.32 (m, 2H) |
| 6 | DMSO-d$_6$; δ 13.50 (s, 1H), 9.70 (br. s., 1H), 8.35 (d, J = 17.17 Hz, 1H), 7.55 (d, J = 2.31 Hz, 1H), 7.51 (d, J = 8.92 Hz, 1H), 7.27 (br. s., 2H), 7.05 (dd, J = 2.31, 8.92 Hz, 1H), 6.78 (d, J = 7.60 Hz, 2H), 3.80 (s, 3H), 2.60-3.59 (m, 8H), 0.99-2.15 (m, 5H) |

DMSO: dimethyl sulfoxide

The compounds 7 to 31 were prepared as described hereinbelow.

Synthesis of compound 7—Methyl 2-{[4-({[(5-methoxy-1H-indazol-3-yl)carbonyl]amino}methyl)piperidin-1-yl]methyl}-1,3-thiazole-4-carboxylate 7a) Tert-butyl 4-({[(5-methoxy-1H-indazol-3-yl)carbonyl]amino}methyl)piperidine-1-carboxylate 1-Hydroxybenzotriazole (HOBt, 24.3 g, 142 mmoles) and N,N'-dicyclohexylcarbodiimide (DCC, 29.3 g, 142 mmoles) were added to a solution of 5-methoxy-1H-indazole-3-carboxylic acid (30 g, 129 mmoles) in DMF (400 mL) at 0° C. After 1 hour, a solution of ethyl[4-(aminomethyl)piperidin-1-yl]acetate (26 g, 129 mmoles) in DMF (250 mL) was added at the same temperature. The mixture was stirred at 0° C. for 2 hours then was left to reach room temperature during the night. The mixture was diluted with EtOAc and the solid was removed by filtration. The solution was extracted three times with hydrochloridric acid (HCl) 2N. The pH of the acid phase was increased (about 13) with 5N NaOH and the solution was extracted three times with dichloromethane (DCM). The organic phase was dried over anhydrous $Na_2SO_4$ and the solvent was filtered and evaporated under reduced pressure providing Tert-butyl 4-({[(5-methoxy-1H-indazol-3-yl)carbonyl]amino}methyl)piperidine-1-carboxylate 7a (96% yield).
MS: 389 m/z $(M+H)^+$.

7b) 5-Methoxy-N-(piperidin-4-ylmethyl)-1H-indazole-3-carboxamide hydrochloride

2 M HCl in $Et_2O$ (1.8 L) was added to a solution of compound 7a (92.8 g, 0.24 moles) in MeOH (500 mL). The mixture was stirred for 3 hours at room temperature then the resulting solid was filtered and dried to give 5-methoxy-N-(piperidin-4-ylmethyl)-1H-indazole-3-carboxamide hydrochloride 7b (61.1 g, 89% yield).
MS: 289 m/z $(M+H)^+$.

Finally, a mixture of compound 7b (637 mg, 1.96 mmoles) and potassium carbonate (813 mg, 5.88 mmoles) in acetonitrile (5 mL) was heated to reflux for 1 hour, then a solution of methyl 2-(chloromethyl)-1,3-thiazole-4-carboxylate (500 mg, 2.6 mmoles) in acetonitrile (5 mL) was added dropwise. The mixture was refluxed overnight then was cooled, diluted with EtOAc and filtered. The resulting solid was washed with water, dried and purified via flash chromatography (silica, from $CHCl_3$ to $CHCl_3$:MeOH 9:1) providing 280 mg (32% yield) of methyl 2-{[4-({[(5-methoxy-1H-indazol-3-yl)carbonyl]amino}methyl)piperidin-1-yl]methyl}-1,3-thiazole-4-carboxylate 7.
$^1$H NMR (300 MHz, DMSO-d6) δ=13.41 (s, 1H), 8.46 (s, 1H), 8.29 (t, J=6.0 Hz, 1H), 7.55 (d, J=2.2 Hz, 1H), 7.50 (d, J=9.1 Hz, 1H), 7.05 (dd, J=2.4, 9.0 Hz, 1H), 3.81 (s, 3H), 3.80 (s, 5H), 3.21 (t, J=6.2 Hz, 2H), 2.89 (d, J=11.3 Hz, 2H), 2.13 (t, J=10.8 Hz, 2H), 1.78-1.54 (m, 3H), 1.37-1.14 (m, 2H)
MS: 444 m/z $(M+H)^+$.

Synthesis of compound 8—2-{[4-({[(5-Methoxy-1H-indazol-3-yl)carbonyl]amino}methyl)piperidin-1-yl]methyl}-1,3-thiazole-4-carboxylic acid To a solution of compound 7 (1.85 mmoles) in MeOH (10 mL) aqueous 1M NaOH (3.7 mL) was added. The solution was refluxed overnight then the organic solvent was removed under vacuum, the residue was diluted with $H_2O$ and the pH was adjusted to 5 by adding 1M HCl. The mixture was kept at 4° C. overnight then the resulting solid was filtered, washed with fresh water and dried under vacuum to give 2-{[4-({[(5-Methoxy-1H-indazol-3-yl)carbonyl]amino}methyl)piperidin-1-yl]methyl}-1,3-thiazole-4-carboxylic acid 8 (43% yield).
$^1$H NMR (300 MHz, DMSO-d6) δ=13.42 (br. s., 1H), 12.91 (br. s., 1H), 8.34 (s, 1H), 8.29 (t, J=6.0 Hz, 1H), 7.56 (d, J=2.2 Hz, 1H), 7.51 (d, J=9.1 Hz, 1H), 7.05 (dd, J=2.6, 9.1 Hz, 1H), 3.87-3.69 (m, 5H), 3.22 (t, J=6.2 Hz, 2H), 2.89 (d, J=11.3 Hz, 2H), 2.12 (t, J=10.6 Hz, 2H), 1.81-1.50 (m, 3H), 1.37-1.11 (m, 2H)
MS: 430 m/z $(M+H)^+$.

Synthesis of compound 9—Methyl 2-{[4-({[(5-methoxy-1H-indazol-3-yl)carbonyl]amino}methyl)piperidin-1-yl]methyl}-1,3-oxazole-4-carboxylate Methyl 2-{[4-({[(5-methoxy-1H-indazol-3-yl)carbonyl]amino}methyl) piperidin-1-yl]methyl}-1,3-oxazole-4-carboxylate 9 was prepared, according to the procedure described for compound 7, using methyl 2-(chloromethyl)-1,3-oxazole-4-carboxylate. Yield: 410 mg, 45%.
$^1$H NMR (300 MHz, DMSO-d6) δ=13.40 (br. s., 1H), 8.80 (s, 1H), 8.26 (t, J=6.2 Hz, 1H), 7.55 (d, J=2.6 Hz, 1H), 7.51 (d, J=9.1 Hz, 1H), 7.05 (dd, J=2.4, 9.0 Hz, 1H), 3.80 (s, 6H), 3.67 (s, 2H), 3.18 (t, J=6.2 Hz, 2H), 2.82 (d, J=11.3 Hz, 2H), 2.14-1.93 (m, 2H), 1.74-1.45 (m, 3H), 1.29-1.10 (m, 2H)
MS: 428 m/z $(M+H)^+$.

Synthesis of compound 10—2-{[4-({[(5-Methoxy-1H-indazol-3-yl)carbonyl]amino}methyl)piperidin-1-yl]methyl}-1,3-oxazole-4-carboxylic acid hydrate 2-{[4-({[(5-Methoxy-1H-indazol-3-yl)carbonyl]amino}methyl) piperidin-1-yl]methyl}-1,3-oxazole-4-carboxylic acid hydrate 10 was prepared, according to the procedure described for compound 8, starting from compound 9. Yield: 238 mg, 82%.
$^1$H NMR (300 MHz, DMSO-d6) δ=13.40 (s, 1H), 12.99 (br. s., 1H), 8.67 (s, 1H), 8.26 (t, J=6.0 Hz, 1H), 7.55 (d, J=2.2 Hz, 1H), 7.50 (d, J=9.5 Hz, 1H), 7.04 (dd, J=2.6, 9.1 Hz, 1H), 3.80 (s, 3H), 3.66 (s, 2H), 3.18 (t, J=6.4 Hz, 2H), 2.82 (d, J=11.0 Hz, 2H), 2.05 (t, J=10.4 Hz, 2H), 1.76-1.44 (m, 3H), 1.33-1.05 (m, 2H)
MS: 414 m/z $(M+H)^+$.

Synthesis of compound 11—Methyl 2-{[4-({[(5-bromo-1H-indazol-3-yl)carbonyl]amino}methyl)piperidin-1-yl]methyl}-1,3-oxazole-4-carboxylate 11a) Tert-butyl 4-({[(5-bromo-1H-indazol-3-yl)carbonyl]amino}methyl)piperidine-1-carboxylate Tert-butyl 4-({[(5-bromo-1H-indazol-3-yl)carbonyl]amino}methyl) piperidine-1-carboxylate 11a was prepared, according to the procedure described for compound 7, from 5-bromo-1H-indazole-3-carboxylic acid and tert-butyl 4-(aminomethyl)piperidine-1-carboxylate. Yield: 40.6 g, 87%
MS: 437 m/z $(M+H)^+$.

11b) 5-Bromo-N-(piperidin-4-ylmethyl)-1H-indazole-3-carboxamide hydrochloride

2M HCl in $Et_2O$ (1.8 L) was added to a solution of compound tert-butyl 4-(aminomethyl)piperidine-1-carboxylate 11a (0.24 moles) in MeOH (500 mL). The mixture was stirred for 3 hours at room temperature then the resulting solid was filtered and dried to give 5-Bromo-N-(piperidin-4-ylmethyl)-1H-indazole-3-carboxamide hydrochloride 11 b (76% yield).

MS: 337 m/z (M+H)$^+$.

Finally, methyl 2-{[4-({[(5-bromo-1H-indazol-3-yl)carbonyl]amino}methyl)piperidin-1-yl]methyl}-1,3-oxazole-4-carboxylate 11 was prepared, according to the procedure described for compound 7, from 11 b and methyl 2-(chloromethyl)-1,3-oxazole-4-carboxylate. Yield: 166 mg, 16%.

$^1$H NMR (300 MHz, DMSO-d6) δ=13.73 (br. s., 1H), 8.80 (s, 1H), 8.42 (t, J=6.0 Hz, 1H), 8.31 (dd, J=0.8, 1.8 Hz, 1H), 7.60 (dd, J=0.8, 8.8 Hz, 1H), 7.52 (dd, J=1.8, 8.8 Hz, 1H), 3.80 (s, 3H), 3.67 (s, 2H), 3.18 (t, J=6.4 Hz, 2H), 2.81 (d, J=11.3 Hz, 2H), 2.13-1.95 (m, 2H), 1.74-1.44 (m, 3H), 1.32-1.06 (m, 2H)

MS: 428 m/z (M+H)$^+$.

Synthesis of compound 12—2-({4-[({[5-(2,3-Difluorophenyl)-1H-indazol-3-yl]carbonyl}amino)methyl]piperidin-1-yl}methyl)-1,3-oxazole-4-carboxylic acid hydrate A solution of compound 11 (0.44 mmoles), (2,3-difluorophenyl)boronic acid (1.77 mmoles), [1,1'-bis(diphenylphosphino)ferrocene]-dichloro-palladium(II) [Pd(dppf)Cl$_2$] (81 mg, 0.11 mmoles) and caesium carbonate (575 mg, 1.76 mmoles) in 1,4-dioxane and water (ratio 3:1, 8 mL) was subjected to microwave irradiation as follows:

Time period=3'; T$_1$=160° C., T$_2$=130° C.; max power 300 W

Time period=45'; T$_1$=160° C., T$_2$=130° C.; max power 300 W

Time period=5'; T$_1$=20° C., T$_2$=15° C.

After one cycle of microwave irradiation, solvents were removed by evaporating under reduce pressure and the reaction mixture was diluted with a solution of methanol (20 mL), filtered over Celite and dried under vacuum. The crude product was filtered on a silica cartridge and washed with chloroform and methanol in a 1:1 ratio. The resulting solid was dissolved in DMSO and purified via preparative HPLC (channel A=CH$_3$CN+0.1% formic acid; channel B=H$_2$O+0.1% formic acid: flow=40 ml/min; gradient=15%-50% of eluent A in 15 minutes), providing 2-({4-[({[5-(2,3-Difluorophenyl)-1H-indazol-3-yl]carbonyl}amino)methyl]piperidin-1-yl}methyl)-1,3-oxazole-4-carboxylic acid hydrate 12 (6% yield).

$^1$H NMR (300 MHz, DMSO-d6) δ=13.70 (s, 1H), 12.99 (br. s., 1H), 8.57 (s, 1H), 8.42 (t, J=6.0 Hz, 1H), 8.34 (d, J=0.7 Hz, 1H), 7.73 (dd, J=0.8, 8.8 Hz, 1H), 7.61 (td, J=1.8, 8.7 Hz, 1H), 7.52-7.21 (m, 3H), 3.64 (s, 2H), 3.20 (t, J=6.2 Hz, 2H), 2.82 (d, J=11.0 Hz, 2H), 2.04 (t, J=10.6 Hz, 2H), 1.73-1.45 (m, 3H), 1.33-1.09 (m, 2H)

MS: 496 m/z (M+H)$^+$.

Synthesis of compound 13—Ethyl 4-{[4-({[(5-methoxy-1H-indazol-3-yl)carbonyl]amino}methyl)piperidin-1-yl]methyl}-1,3-thiazole-2-carboxylate Ethyl 4-{[4-({[(5-methoxy-1H-indazol-3-yl)carbonyl]amino}methyl) piperidin-1-yl]methyl}-1,3-thiazole-2-carboxylate 13 was prepared, according to the procedure described for compound 7, using ethyl 4-(chloromethyl)-1,3-thiazole-2-carboxylate. Yield: 45 mg, 11%.

$^1$H NMR (300 MHz, DMSO-d6) δ=13.39 (s, 1H), 8.26 (t, J=6.0 Hz, 1H), 7.86 (s, 1H), 7.55 (d, J=2.2 Hz, 1H), 7.50 (d, J=8.8 Hz, 1H), 7.04 (dd, J=2.2, 8.8 Hz, 1H), 4.37 (q, J=7.0 Hz, 2H), 3.80 (s, 3H), 3.64 (s, 2H), 3.19 (t, J=6.2 Hz, 2H), 2.85 (d, J=11.3 Hz, 2H), 1.98 (t, J=10.6 Hz, 2H), 1.79-1.45 (m, 3H), 1.33 (t, J=7.1 Hz, 3H), 1.29-0.96 (m, 2H)

MS: 458 m/z (M+H)$^+$.

Synthesis of compound 14—Methyl 2-{[4-({[(5-methoxy-1H-indazol-3-yl)carbonyl]amino}methyl)piperidin-1-yl]methyl}furan-3-carboxylate Methyl 2-{[4-({[(5-methoxy-1H-indazol-3-yl)carbonyl]amino}methyl) piperidin-1-yl]methyl}furan-3-carboxylate 14 was prepared, according to the procedure described for compound 7, using methyl 2-(chloromethyl)furan-3-carboxylate. Yield: 120 mg, 13%.

$^1$H NMR (300 MHz, DMSO-d6) δ=13.39 (s, 1H), 8.23 (t, J=6.0 Hz, 1H), 7.70 (d, J=2.2 Hz, 1H), 7.54 (d, J=2.6 Hz, 1H), 7.50 (d, J=8.4 Hz, 1H), 7.04 (dd, J=2.4, 9.0 Hz, 1H), 6.70 (d, J=2.2 Hz, 1H), 3.83 (s, 2H), 3.80 (s, 3H), 3.76 (s, 3H), 3.17 (t, J=6.4 Hz, 2H), 2.80 (d, J=11.3 Hz, 2H), 2.10-1.88 (m, 2H), 1.70-1.42 (m, 3H), 1.31-1.02 (m, 2H)

MS: 427 m/z (M+H)$^+$.

Synthesis of compound 15—Ethyl 5-{[4-({[(5-bromo-1H-indazol-3-yl)carbonyl]amino}methyl)piperidin-1-yl]methyl}furan-2-carboxylate Ethyl 5-{[4-({[(5-bromo-1H-indazol-3-yl)carbonyl]amino}methyl) piperidin-1-yl]methyl}furan-2-carboxylate 15 was prepared, according to the procedure described for compound 7, from 11b and ethyl 5-(chloromethyl)furan-2-carboxylate. Yield: 300 mg, 62%.

$^1$H NMR (300 MHz, DMSO-d6) δ=13.73 (br. s., 1H), 8.41 (t, J=6.04 Hz, 1H), 8.32 (dd, J=0.73, 1.83 Hz, 1H), 7.57-7.65 (m, 1H), 7.45-7.56 (m, 1H), 7.21 (d, J=3.66 Hz, 1H), 6.48 (d, J=3.66 Hz, 1H), 4.27 (q, J=7.32 Hz, 2H), 3.53 (s, 2H), 3.19 (t, J=6.40 Hz, 2H), 2.81 (d, J=11.34 Hz, 2H), 1.82-2.09 (m, 2H), 1.64 (d, J=12.44 Hz, 3H), 1.02-1.36 (m, 5H)

MS: 489 m/z (M+H)$^+$.

Synthesis of compound 16—5-({4-[({[5-(2-Methoxypyridin-3-yl)-1H-indazol-3-yl]carbonyl}amino)methyl]piperidin-1-yl}methyl)furan-2-carboxylic acid hydrate 5-({4-[({[5-(2-Methoxypyridin-3-yl)-1H-indazol-3-yl]carbonyl}amino)methyl]piperidin-1-yl}methyl)furan-2-carboxylic acid hydrate 16 was prepared, according to the procedure described for compound 12, from compound 15 and (2-methoxypyridin-3-yl)boronic acid and using the following preparative HPLC parameters for the purification: channel A=CH$_3$CN+0.1% formic acid; channel B=H$_2$O+0.1% formic acid: flow=40 ml/min; gradient=10%-45% of eluent A in 15 minutes. Yield: 14 mg, 5%.

$^1$H NMR (300 MHz, DMSO-d6) δ 13.62 (br. s., 1H), 8.36 (t, J=6.04 Hz, 1H), 8.28 (s, 1H), 8.19 (dd, J=1.83, 5.12 Hz, 1H), 7.77 (dd, J=2.20, 7.32 Hz, 1H), 7.65 (dd, J=0.80, 8.80 Hz, 1H), 7.58 (dd, J=1.80, 8.80 Hz, 1H), 7.11 (dd, J=5.12, 7.32 Hz, 1H), 6.84 (br. s., 1H), 6.31 (d, J=2.93 Hz, 1H), 3.89 (s, 3H), 3.47 (s, 2H), 3.19 (t, J=6.22 Hz, 2H), 2.99 (s, 1H), 2.82 (d, J=10.98 Hz, 2H), 1.83-2.04 (m, 2H), 1.41-1.75 (m, 3H), 1.06-1.34 (m, 2H)

MS: 490 m/z (M+H)$^+$.

Synthesis of compound 17—5-({4-[({[5-(6-Methoxypyridin-3-yl)-1H-indazol-3-yl]carbonyl}amino)methyl]piperidin-1-yl}methyl)uran-2-carboxylic acid hydrate 5-({4-[({[5-(6-Methoxypyridin-3-yl)-1H-indazol-3-yl]carbonyl}amino)methyl]piperidin-1-yl}methyl)furan-2-carboxylic acid hydrate 17 was prepared, according to the procedure described for compound 12, from compound 15 and (6-methoxypyridin-3-yl)boronic acid and using the following preparative HPLC parameters for the purification: channel A=CH$_3$CN+0.1% formic acid; channel B=H$_2$O+0.1% formic acid: flow=40 ml/min; gradient=10%-45% of eluent A in 15 minutes. Yield: 23 mg, 8%.

$^1$H NMR (300 MHz, DMSO-d6) δ 13.65 (br. s., 1H), 8.48 (d, J=2.02 Hz, 1H), 8.39 (t, J=6.06 Hz, 1H), 8.34 (s, 1H), 7.96-8.07 (m, 1H), 7.70 (d, J=1.21 Hz, 2H), 7.03 (d, J=3.23 Hz, 1H), 6.94 (d, J=8.07 Hz, 1H), 6.40 (d, J=3.23 Hz, 1H), 3.92 (s, 3H), 3.51 (s, 2H), 3.21 (t, J=6.26 Hz, 2H), 2.83 (d, J=10.90 Hz, 2H), 1.98 (t, J=10.90 Hz, 2H), 1.48-1.78 (m, 3H), 1.07-1.34 (m, 2H)

MS: 490 m/z (M+H)$^+$.

Synthesis of compound 18—5-({4-[({[5-(4-Methoxyphenyl)-1H-indazol-3-yl]carbonyl}amino)methyl]piperidin-1-yl}methyl)furan-2-carboxylic acid hydrate 5-({4-[({[5-(4-Methoxyphenyl)-1H-indazol-3-yl]carbonyl}amino)methyl]piperidin-1-yl}methyl)furan-2-carboxylic acid hydrate 18 was prepared, according to the procedure described for compound 12, from compound 15 and (4-methoxyphenyl)boronic acid and using the following preparative HPLC parameters for the purification: channel A=CH$_3$CN+0.1% formic acid; channel B=H$_2$O+0.1% formic acid: flow=40 ml/min; gradient=15%-50% of eluent A in 15 minutes. Yield: 14 mg, 5%.

$^1$H NMR (300 MHz, DMSO-d6) δ 13.55 (s, 1H), 8.27-8.41 (m, 2H), 7.64-7.72 (m, 2H), 7.61 (d, J=8.88 Hz, 2H), 7.05 (d, J=8.88 Hz, 2H), 6.96 (br. s., 1H), 6.37 (d, J=3.23 Hz, 1H), 3.81 (s, 3H), 3.49 (s, 2H), 3.20 (t, J=6.26 Hz, 2H), 2.82 (d, J=10.90 Hz, 2H), 1.86-2.05 (m, 2H), 1.66 (d, J=12.11 Hz, 3H), 1.09-1.33 (m, 2H)

MS: 489 m/z (M+H)$^+$.

Synthesis of compound 19—5-({4-[({[5-(2,3-Difluorophenyl)-1H-indazol-3-yl]carbonyl}amino)methyl]piperidin-1-yl}methyl)furan-2-carboxylic acid 5-({4-[({[5-(2,3-Difluorophenyl)-1H-indazol-3-yl]carbonyl}amino)methyl]piperidin-1-yl}methyl)furan-2-carboxylic acid 19 was prepared, according to the procedure described for compound 12, from compound 15 and (2,3-difluorophenyl)boronic acid and using the following preparative HPLC parameters for the purification: channel A=CH$_3$CN+0.1% formic acid; channel B=H$_2$O+0.1% formic acid: flow=40 ml/min; gradient=15%-50% of eluent A in 15 minutes. Yield: 32 mg, 11%.

$^1$H NMR (300 MHz, DMSO-d6) δ 13.74 (br. s., 1H), 8.42 (t, J=5.65 Hz, 1H), 8.35 (s, 1H), 7.69-7.80 (m, 1H), 7.55-7.67 (m, 1H), 7.21-7.54 (m, 3H), 7.05 (d, J=3.23 Hz, 1H), 6.41 (d, J=3.23 Hz, 1H), 3.52 (s, 2H), 3.20 (t, J=6.06 Hz, 2H), 2.83 (d, J=10.50 Hz, 2H), 1.98 (t, J=10.70 Hz, 2H), 1.42-1.79 (m, 3H), 1.04-1.35 (m, 2H)

MS: 495 m/z (M+H)$^+$.

Synthesis of compound 20—5-({4-[({[5-(2-Fluorophenyl)-1H-indazol-3-yl]carbonyl}amino)methyl]piperidin-1-yl}methyl)furan-2-carboxylic acid hydrate 5-({4-[({[5-(2-Fluorophenyl)-1H-indazol-3-yl]carbonyl}amino)methyl]piperidin-1-yl}methyl)furan-2-carboxylic acid hydrate 20 was prepared, according to the procedure described for compound 12, from compound 15 and (2-fluorophenyl)boronic acid and using the following preparative HPLC parameters for the purification: channel A=CH$_3$CN+0.1% formic acid; channel B=H$_2$O+0.1% formic acid: flow=40 ml/min; gradient=10%-45% of eluent A in 15 minutes. Yield: 20 mg, 7%.

$^1$H NMR (300 MHz, DMSO-d6) δ 13.66 (br. s., 1H), 8.39 (t, J=6.04 Hz, 1H), 8.32 (s, 1H), 7.65-7.76 (m, 1H), 7.50-7.63 (m, 2H), 7.38-7.50 (m, 1H), 7.23-7.38 (m, 2H), 7.08 (d, J=3.29 Hz, 1H), 6.43 (d, J=3.29 Hz, 1H), 3.52 (s, 2H), 3.20 (t, J=6.22 Hz, 2H), 2.82 (d, J=10.98 Hz, 2H), 1.98 (t, J=10.79 Hz, 2H), 1.44-1.79 (m, 3H), 1.02-1.38 (m, 2H)

MS: 477 m/z (M+H)$^+$.

Synthesis of compound 21—5-({4-[({[5-(4-Methoxypyridin-3-yl)-1H-indazol-3-yl]carbonyl}amino)methyl]piperidin-1-yl}methyl)furan-2-carboxylic acid formate 5-({4-[({[5-(4-Methoxypyridin-3-yl)-1H-indazol-3-yl]carbonyl}amino)methyl]piperidin-1-yl}methyl)furan-2-carboxylic acid formate 21 was prepared, according to the procedure described for compound 12, from compound 15 and (4-methoxypyridin-3-yl)boronic acid and using the following preparative HPLC parameters for the purification: channel A=CH$_3$CN+0.1% formic acid; channel B=H$_2$O+0.1% formic acid: flow=40 ml/min; gradient=2%-40% of eluent A in 15 minutes. Yield: 40 mg, 14%.

$^1$H NMR (300 MHz, DMSO-d6) δ 13.61 (br. s., 1H), 8.47 (d, J=5.85 Hz, 1H), 8.31-8.43 (m, 2H), 8.24 (s, 1H), 7.66 (d, J=8.78 Hz, 1H), 7.53 (dd, J=1.46, 8.42 Hz, 1H), 7.18 (d, J=5.49 Hz, 1H), 7.09 (d, J=3.29 Hz, 1H), 6.43 (d, J=3.29 Hz, 1H), 3.86 (s, 3H), 3.54 (s, 2H), 3.19 (t, J=6.04 Hz, 2H), 2.83 (d, J=10.98 Hz, 2H), 1.99 (t, J=10.79 Hz, 2H), 1.44-1.79 (m, 3H), 0.98-1.36 (m, 2H)

MS: 490 m/z (M+H)$^+$.

Synthesis of compound 22—5-{[4-({[(5-Bromo-1H-indazol-3-yl)carbonyl]amino}methyl)piperidin-1-yl]methyl}furan-2-carboxylic acid 5-{[4-({[(5-Bromo-1H-indazol-3-yl)carbonyl]amino}methyl)piperidin-1-yl]methyl}furan-2-carboxylic acid 22 was prepared, according to the procedure described for compound 8, starting from compound 15 and using EtOH as solvent. Yield: 264 mg, 98%.

$^1$H NMR (300 MHz, DMSO-d6) δ 13.78 (br. s., 1H), 8.43 (t, J=5.85 Hz, 1H), 8.32 (d, J=1.21 Hz, 1H), 7.61 (d, J=8.80 Hz, 1H), 7.53 (dd, J=2.00, 8.80 Hz, 1H), 7.11 (d, J=3.63 Hz, 1H), 6.45 (d, J=3.23 Hz, 1H), 3.57 (s, 2H), 3.19 (t, J=6.26 Hz, 2H), 2.85 (d, J=11.30 Hz, 2H), 2.02 (t, J=10.90 Hz, 2H), 1.45-1.77 (m, 3H), 1.08-1.37 (m, 2H)

MS: 461 m/z (M+H)$^+$.

Synthesis of compound 23—Ethyl 5-{[4-({[(5-methoxy-1H-indazol-3-yl)carbonyl]amino}methyl)piperidin-1-yl]methyl}furan-2-carboxylate Ethyl 5-{[4-({[(5-methoxy-1H-indazol-3-yl)carbonyl]amino}methyl) piperidin-1-yl]methyl}furan-2-carboxylate 23 was prepared, according to the procedure described for compound 7, starting from ethyl 5-(chloromethyl)furan-2-carboxylate. Yield: 290 mg, 71%.

$^1$H NMR (300 MHz, DMSO-d6) δ 13.37 (br. s., 1H), 8.25 (t, J=6.04 Hz, 1H), 7.42-7.60 (m, 2H), 7.21 (d, J=3.29 Hz, 1H), 6.97-7.12 (m, 1H), 6.48 (d, J=3.29 Hz, 1H), 4.26 (q,

J=7.32 Hz, 2H), 3.80 (s, 3H), 3.53 (s, 2H), 3.18 (t, J=6.22 Hz, 2H), 2.81 (d, J=11.34 Hz, 2H), 1.87-2.05 (m, 2H), 1.46-1.73 (m, 3H), 1.28 (t, J=6.95 Hz, 3H), 1.01-1.41 (m, 2H)

MS: 441 m/z (M+H)$^+$.

Synthesis of compound 24—5-{[4-({[(5-Methoxy-1H-indazol-3-yl)carbonyl]amino}methyl)piperidin-1-yl]methyl}furan-2-carboxylic acid 5-{[4-({[(5-Methoxy-1H-indazol-3-yl)carbonyl]amino}methyl) piperidin-1-yl]methyl}furan-2-carboxylic acid 24 was prepared, according to the procedure described for compound 8, starting from compound 23 and using EtOH as solvent. Yield: 64 mg, 84%.

$^1$H NMR (300 MHz, DMSO-d6) δ 12.78-14.43 (m, 1H), 8.26 (t, J=6.04 Hz, 1H), 7.55 (d, J=2.56 Hz, 1H), 7.52 (d, J=9.15 Hz, 1H), 7.04 (dd, J=2.60, 9.10 Hz, 1H), 6.91 (d, J=3.29 Hz, 1H), 6.35 (d, J=3.29 Hz, 1H), 4.04 (br. s., 1H), 3.80 (s, 3H), 3.50 (s, 2H), 3.18 (t, J=6.22 Hz, 2H), 2.83 (d, J=11.34 Hz, 2H), 1.97 (t, J=10.79 Hz, 2H), 1.47-1.73 (m, 3H), 1.04-1.33 (m, 2H)

MS: 413 m/z (M+H)$^+$.

Synthesis of compound 25—N-[(1-{2-[(2R,6S)-2,6-dimethyl morpholin-4-yl]ethyl}piperidin-4-yl)methyl]-5-methoxy-1H-indazole-3-carboxamide A mixture of compound 7b (8 g, 24.6 mmoles) and potassium carbonate (17 g, 123 mmoles) in acetone (250 mL) was refluxed for 1 hour, then (2R,6S)-4-(2-chloroethyl)-2,6-dimethylmorpholine (25.9 mmoles) was added dropwise. The mixture was refluxed overnight then was cooled and filtered. The resulting solid was dried and purified via preparative HPLC (channel A=CH$_3$CN+0.1% formic acid; channel B=H$_2$O+0.1% formic acid: flow=40 ml/min; gradient=10%-45% of eluent A in 15 minutes) providing N-[(1-{2-[(2R,6S)-2,6-dimethylmorpholin-4-yl]ethyl}piperidin-4-yl)methyl]-5-methoxy-1H-indazole-3-carboxamide 25 (48.3% yield)

$^1$H NMR (300 MHz, DMSO-d6) δ=13.40 (s, 1H), 8.30-8.14 (t, J=6.11 Hz, 1H), 7.58-7.53 (d, J=1.98 Hz, 1H), 7.53-7.46 (dd, J=8.92, 0.66 Hz, 1H), 7.11-6.96 (dd, J=8.92, 2.31 Hz, 1H), 3.80 (s, 3H), 3.57-3.43 (m, 2H), 3.21-3.11 (t, J=6.28 Hz, 2H), 2.92-2.77 (d, J=11.23 Hz, 2H), 2.76-2.63 (d, J=10.24 Hz, 2H), 2.44-2.26 (m, 4H), 1.97-1.77 (t, J=10.90 Hz, 2H), 1.71-1.46 (t, J=10.73 Hz, 4H), 1.27-1.07 (m, 3H), 1.06-0.94 (d, J=6.28 Hz, 6H)

LC-MS: 430.28 (MH+)

Synthesis of compound 26—N-[(1-{3-[(2R,6S)-2,6-dimethyl morpholin-4-yl]propyl}piperidin-4-yl)methyl]-5-methoxy-1H-indazole-3-carboxamide N-[(1-{3-[(2R,6S)-2,6-dimethylmorpholin-4-yl]propyl}piperidin-4-yl) methyl]-5-methoxy-1H-indazole-3-carboxamide 26, was prepared, according to the procedure described for compound 25, using (2R,6S)-4-(3-chloropropyl)-2,6-dimethylmorpholine and methanol as solvent. Yield=91 mg (59.1%).

$^1$H NMR (300 MHz, DMSO-d6) δ=12.12 (s, 1H), 7.80-7.62 (d, J=2.20 Hz, 1H), 7.40-7.32 (d, J=9.15 Hz, 1H), 7.27-7.18 (t, J=6.04 Hz, 1H), 7.07-6.99 (dd, J=9.15, 2.20 Hz, 1H), 3.89-3.78 (s, 3H), 3.76-3.53 (m, 2H), 3.47-3.30 (t, J=6.22 Hz, 2H), 3.07-2.93 (m, 2H), 2.75-2.68 (d, J=10.98 Hz, 2H), 2.45-2.24 (m, 4H), 2.07-1.88 (t, J=10.79 Hz, 2H), 1.83-1.59 (m, 7H), 1.53-1.35 (m, 2H), 1.18-1.05 (d, J=6.22 Hz, 6H)

LC-MS: 444.30 (MH+)

Synthesis of compound 27—5-methoxy-N-({1-[2-(3-methyl cyclohexyl)ethyl]piperidin-4-yl}methyl)-1H-indazole-3-carboxamide A solution of compound 11b (420 mg, 1.46 mmol) in DMF (45 ml) and triethylamine (0.61 ml, 4.4 mmol) was stirred at 80° C. for 1 h and then was treated with 1-(2-bromoethyl)-3-methylcyclohexane (300 mg, 1.46 mmol). The mixture was stirred overnight at the same temperature. The reaction was then cooled to room temperature and the solvent was removed by evaporation at reduced pressure. The crude 5-methoxy-N-({1-[2-(3-methylcyclohexyl)ethyl]piperidin-4-yl}methyl)-1H-indazole-3-carboxamide 27 was purified by flash chromatography on silica gel, using a 9/1 mixture of CH$_3$Cl/CH$_3$OH as eluent. Yield=45 mg (18.0%).

1H NMR (300 MHz, DMSO-d6) δ=13.41 (s, 1H), 8.30-8.20 (t, J=6.11 Hz, 1H), 7.58-7.53 (d, J=2.31 Hz, 1H), 7.53-7.47 (d, J=8.59 Hz, 1H), 7.08-7.02 (dd, J=8.92, 2.32 Hz, 1H), 3.80 (s, 3H), 3.23-3.13 (t, J=6.28 Hz, 2H), 2.90-2.78 (d, J=10.57 Hz, 2H), 2.35-2.20 (m, 2H), 1.97-1.05 (m, 17H), 0.90-0.45 (m, 5H)

LC-MS: 413.29 (MH+)

Synthesis of compound 28—4-{[4-({[(5-methoxy-1H-indazol-3-yl)carbonyl]amino}methyl)piperidin-1-yl]methyl}pyridine-2-carboxylic acid 4-{[4-({[(5-methoxy-1H-indazol-3-yl)carbonyl]amino}methyl) piperidin-1-yl]methyl}pyridine-2-carboxylic acid 28, was prepared, according to the procedure described for compound 25, using methyl 4-(chloromethyl)pyridine-2-carboxylate as reagent and CH$_3$CN as solvent. Yield=335 mg (16%).

$^1$H NMR (300 MHz, DMSO-d6) δ=13.25 (s, 1H), 8.54 (d, J=4.8 Hz, 1H), 8.27 (t, J=6.0 Hz, 1H), 7.93 (s, 1H), 7.56 (d, J=2.2 Hz, 1H), 7.51 (d, J=9.5 Hz, 1H), 7.43 (d, J=4.0 Hz, 1H), 7.04 (dd, J=2.2, 9.5 Hz, 1H), 3.80 (s, 3H), 3.53 (s, 2H), 3.20 (t, J=6.0 Hz, 2H), 2.78 (d, J=11.0 Hz, 2H), 1.96 (t, J=10.6 Hz, 2H), 1.75-1.45 (m, 3H), 1.35-1.16 (m, 2H)

Synthesis of compound 29—Sodium 5-{[4-({[(5-methoxy-1H-indazol-3-yl)carbonyl]amino}methyl) piperidin-1-yl]methyl}pyridine-2-carboxylate 29a) Methyl 5-{[4-({[(5-methoxy-1H-indazol-3-yl)carbonyl]amino}methyl)piperidin-1-yl]methyl}pyridine-2-carboxylate Methyl 5-{[4-({[(5-methoxy-1H-indazol-3-yl)carbonyl]amino}methyl) piperidin-1-yl]methyl}pyridine-2-carboxylate 29a, was prepared according to the procedure described for compound 25 using methyl 5-(chloromethyl)pyridine-2-carboxylate as reagent and CH$_3$CN as solvent and used for the subsequent step without further purification.

Then, a solution of crude methyl 5-{[4-({[(5-methoxy-1H-indazol-3-yl)carbonyl]amino}methyl)piperidin-1-yl]methyl}pyridine-2-carboxylate 29a (1.2 g, 2.7 mmol) in ethanol (10 ml) was treated with a solution of NaOH (0.22 g, 5.5 mmol) in water (10 ml) at reflux for 3 h. The mixture is cooled to room temperature and solvents were evaporated under reduced pressure. The sodium 5-{[4-({[(5-methoxy-1H-indazol-3-yl)carbonyl]amino}methyl)piperidin-1-yl]methyl}pyridine-2-carboxylate 29 was crystallized by a mixture of ethanol/ethyl acetate (1.09 g, 91%).

1H NMR (300 MHz, DMSO-d6) δ=13.86 (br. s., 1H), 8.37 (d, J=1.2 Hz, 1H), 8.24 (t, J=6.1 Hz, 1H), 7.91 (d, J=8.1 Hz, 1H), 7.65 (dd, J=2.0, 8.1 Hz, 1H), 7.61-7.48 (m, 2H), 7.01 (dd, J=2.5, 8.8 Hz, 1H), 3.79 (s, 3H), 3.47 (s, 2H), 3.19 (t, J=6.1 Hz, 2H), 2.77 (d, J=10.9 Hz, 2H), 1.91 (t, J=10.9 Hz, 2H), 1.65 (s, 3H), 1.35-1.07 (m, 2H)

Synthesis of compound 30—N-({1-[(5-carbamoyl-1,2,4-oxa diazol-3-yl)methyl]piperidin-4-yl}methyl)-5-methoxy-1H-indazole-3-carboxamide N-({1-[(5-carbamoyl-1,2,4-oxadiazol-3-yl)methyl]piperidin-4-yl}methyl)-5-methoxy-1H-indazole-3-carboxamide 30, was prepared, according to the procedure described for compound 25, using ethyl 3-(chloromethyl)-1,2,4-oxadiazole-5-carboxylate as reagent and CH₃CN as solvent. Yield=80 mg (4%).

¹H NMR (300 MHz, DMSO-d6) δ=13.18 (br. s., 1H), 8.70 (br. s., 1H), 8.32 (br. s., 1H), 8.26 (t, J=6.2 Hz, 1H), 7.55 (d, J=1.8 Hz, 1H), 7.50 (dd, J=0.7, 9.1 Hz, 1H), 7.05 (dd, J=1.8, 9.1 Hz, 1H), 3.80 (s, 3H), 3.69 (s, 2H), 3.19 (t, J=6.2 Hz, 2H), 2.86 (d, J=11.0 Hz, 2H), 2.19-1.93 (m, 2H), 1.82-1.39 (m, 3H), 1.33-1.07 (m, 2H)

Synthesis of compound 31—N-({1-[2-(4-nitrophenyl)ethyl]piperidin-4-yl}methyl)-1H-indazole-3-carboxamide hydrochloride A mixture of 7H,14H-pyrazino[1,2-b:4,5-b']diindazole-7,14-dione (8.2 g, 28.5 mmol), 1-{1-[2-(4-nitrophenyl)ethyl]piperidin-4-yl}methanamine (15 g, 57 mmol) in toluene (300 ml) was stirred at room temperature over night. The solid so obtained was filtered, dissolved with 2N HCl (100 ml) and washed with diethylether (3×150 ml). The acid phase was basified with NaOH and extracted with DCM (3×200 ml). The solvent was removed by vacuum and the residue was then poured in THF (30 ml) and treated with 1.25 M HCl in MeOH. The crude, solid N-({1-[2-(4-nitrophenyl)ethyl]piperidin-4-yl}methyl)-1H-indazole-3-carboxamide hydrochloride 31 so obtained was filtered and crystallized from EtOH.

¹H NMR (300 MHz, DMSO-d6) δ=13.70 (s, 1H), 10.82 (br. s., 1H), 8.55 (t, J=6.1 Hz, 1H), 8.30-8.10 (m, 3H), 7.67-7.52 (m, 3H), 7.41 (ddd, J=1.2, 7.0, 8.4 Hz, 1H), 7.24 (ddd, J=0.8, 7.0, 8.0 Hz, 1H), 3.57 (d, J=11.7 Hz, 2H), 3.48-3.15 (m, 6H), 3.04-2.83 (m, 2H), 1.90 (d, J=11.5 Hz, 3H), 1.75-1.50 (m, 2H)

The following Table 1A summarizes the chemical name and structure of the above described compounds 7-31.

TABLE 1A

| | IUPAC name | Structure |
|---|---|---|
| 7 | Methyl 2-{[4-({[(5-methoxy-1H-indazol-3-yl)carbonyl]amino}methyl)piperidin-1-yl]methyl}-1,3-thiazole-4-carboxylate | 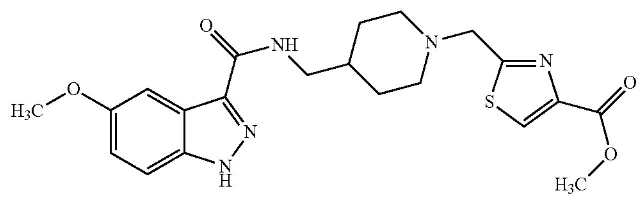 |
| 8 | 2-{[4-({[(5-Methoxy-1H-indazol-3-yl)carbonyl]amino}methyl)piperidin-1-yl]methyl}-1,3-thiazole-4-carboxylic acid | 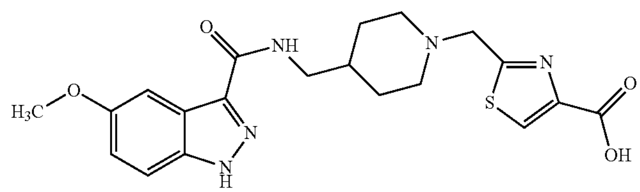 [SMILES: COc1ccc2[nH]nc(C(=O)NCC3CCN(Cc4nc(C(=O)O)cs4)CC3)c2c1] |
| 9 | Methyl 2-{[4-({[(5-methoxy-1H-indazol-3-yl)carbonyl]amino}methyl)piperidin-1-yl]methyl}-1,3-oxazole-4-carboxylate | 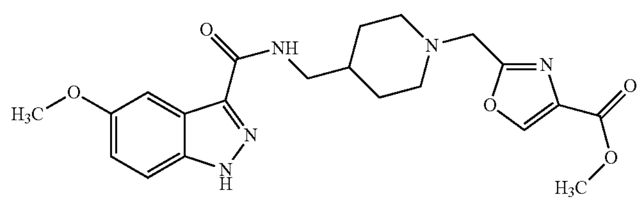 [SMILES: COC(=O)c1coc(CN2CCC(CNC(=O)c3n[nH]c4ccc(OC)cc34)CC2)n1] |
| 10 | 2-{[4-({[(5-Methoxy-1H-indazol-3-yl)carbonyl]amino}methyl)piperidin-1-yl]methyl}-1,3-oxazole-4-carboxylic acid hydrate | 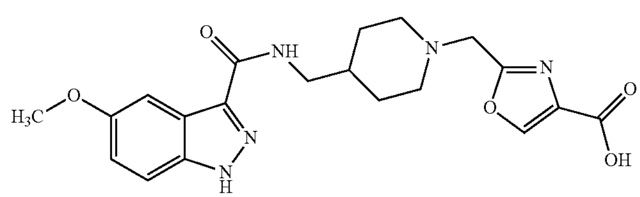 [SMILES: COc1ccc2[nH]nc(C(=O)NCC3CCN(Cc4nc(C(=O)O)co4)CC3)c2c1] |
| 11 | Methyl 2-{[4-({[(5-bromo-1H-indazol-3-yl)carbonyl]amino}methyl)piperidin-1-yl]methyl}-1,3-oxazole-4-carboxylate | 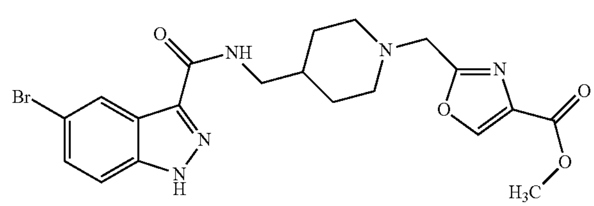 [SMILES: COC(=O)c1coc(CN2CCC(CNC(=O)c3n[nH]c4ccc(Br)cc34)CC2)n1] |

TABLE 1A-continued

| | IUPAC name | Structure |
|---|---|---|
| 12 | 2-({4-[({[5-(2,3-Difluorophenyl)-1H-indazol-3-yl]carbonyl}amino)methyl]piperidin-1-yl}methyl)-1,3-oxazole-4-carboxylic acid hydrate | 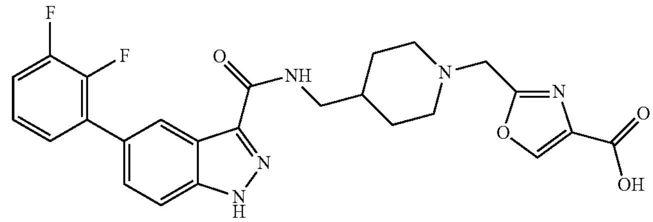 [SMILES: O=C(O)c1coc(CN2CCC(CNC(=O)c3n[nH]c4ccc(-c5cccc(F)c5F)cc34)CC2)n1] |
| 13 | Ethyl 4-{[4-({[(5-methoxy-1H-indazol-3-yl)carbonyl]amino}methyl)piperidin-1-yl]methyl}-1,3-thiazole-2-carboxylate | 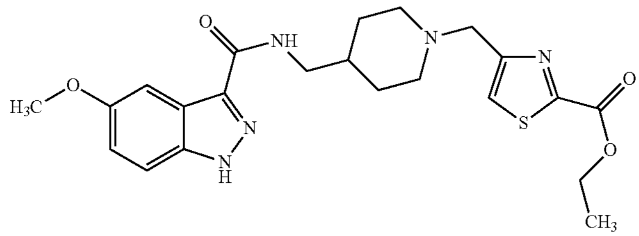 [SMILES: CCOC(=O)c1nc(CN2CCC(CNC(=O)c3n[nH]c4ccc(OC)cc34)CC2)cs1] |
| 14 | Methyl 2-{[4-({[(5-methoxy-1H-indazol-3-yl)carbonyl]amino}methyl)piperidin-1-yl]methyl}furan-3-carboxylate | 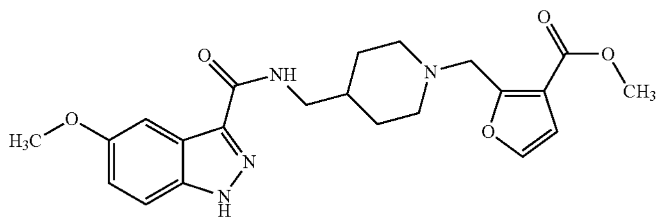 |
| 15 | Ethyl 5-{[4-({[(5-bromo-1H-indazol-3-yl)carbonyl]amino}methyl)piperidin-1-yl]methyl}furan-2-carboxylate | 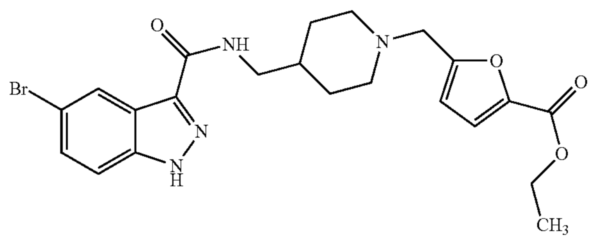 [SMILES: CCOC(=O)c1ccc(CN2CCC(CNC(=O)c3n[nH]c4ccc(Br)cc34)CC2)o1] |
| 16 | 5-({4-[({[5-(2-Methoxypyridin-3-yl)-1H-indazol-3-yl]carbonyl}amino)methyl]piperidin-1-yl}methyl)furan-2-carboxylic acid hydrate | 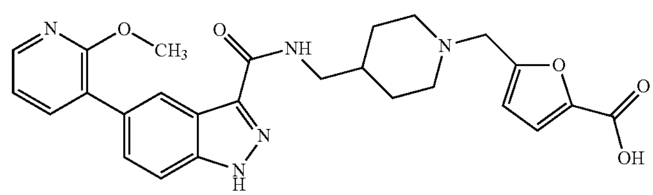 [SMILES: COc1ncccc1-c1ccc2[nH]nc(C(=O)NCC3CCN(Cc4ccc(C(=O)O)o4)CC3)c2c1] |
| 17 | 5-({4-[({[5-(6-Methoxypyridin-3-yl)-1H-indazol-3-yl]carbonyl}amino)methyl]piperidin-1-yl}methyl)furan-2-carboxylic acid hydrate | 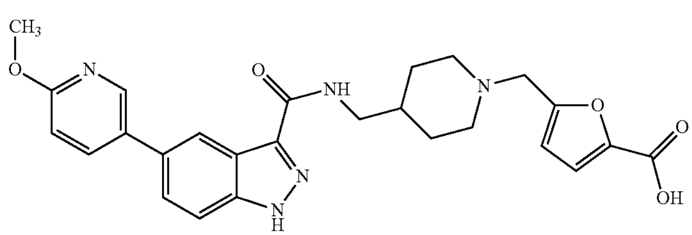 [SMILES: COc1ccc(-c2ccc3[nH]nc(C(=O)NCC4CCN(Cc5ccc(C(=O)O)o5)CC4)c3c2)cn1] |
| 18 | 5-({4-[({[5-(4-Methoxyphenyl)-1H-indazol-3-yl]carbonyl}amino)methyl]piperidin-1-yl}methyl)furan-2-carboxylic acid hydrate | 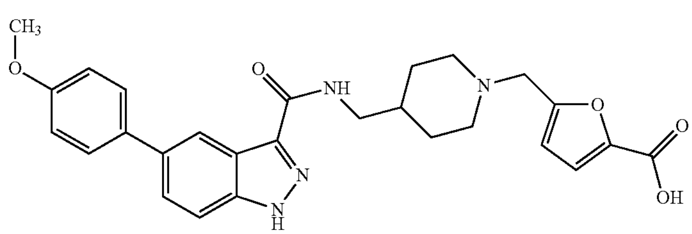 [SMILES: COc1ccc(-c2ccc3[nH]nc(C(=O)NCC4CCN(Cc5ccc(C(=O)O)o5)CC4)c3c2)cc1] |

TABLE 1A-continued

| | IUPAC name | Structure |
|---|---|---|
| 19 | 5-({4-[({[5-(2,3-Difluorophenyl)-1H-indazol-3-yl]carbonyl}amino)methyl]piperidin-1-yl}methyl)furan-2-carboxylic acid | 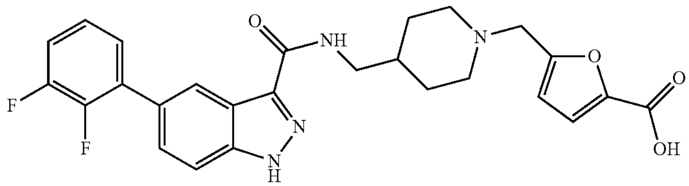 [SMILES: O=C(O)c1ccc(CN2CCC(CNC(=O)c3n[nH]c4ccc(-c5cccc(F)c5F)cc34)CC2)o1] |
| 20 | 5-({4-[({[5-(2-Fluorophenyl)-1H-indazol-3-yl]carbonyl}amino)methyl]piperidin-1-yl}methyl)furan-2-carboxylic acid hydrate | 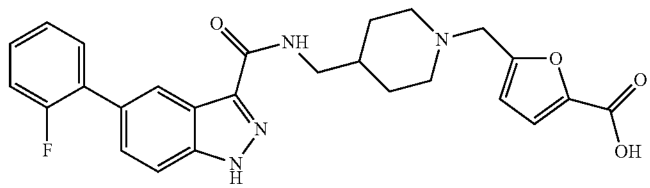 [SMILES: O=C(O)c1ccc(CN2CCC(CNC(=O)c3n[nH]c4ccc(-c5ccccc5F)cc34)CC2)o1] |
| 21 | 5-({4-[({[5-(4-Methoxypyridin-3-yl)-1H-indazol-3-yl]carbonyl}amino)methyl]piperidin-1-yl}methyl)furan-2-carboxylic acid formate | 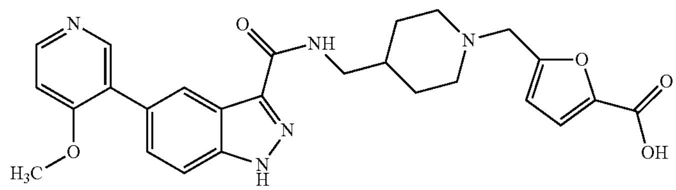 [SMILES: COc1ccncc1-c1ccc2[nH]nc(C(=O)NCC3CCN(Cc4ccc(C(=O)O)o4)CC3)c2c1] |
| 22 | 5-{[4-({[(5-Bromo-1H-indazol-3-yl)carbonyl]amino}methyl)piperidin-1-yl]methyl}furan-2-carboxylic acid | 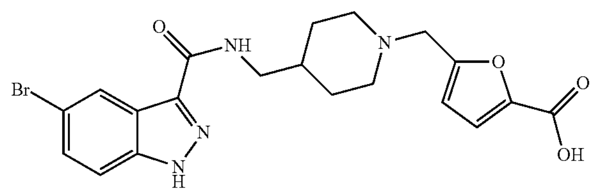 [SMILES: O=C(O)c1ccc(CN2CCC(CNC(=O)c3n[nH]c4ccc(Br)cc34)CC2)o1] |
| 23 | Ethyl 5-{[4-({[(5-methoxy-1H-indazol-3-yl)carbonyl]amino}methyl)piperidin-1-yl]methyl}furan-2-carboxylate | 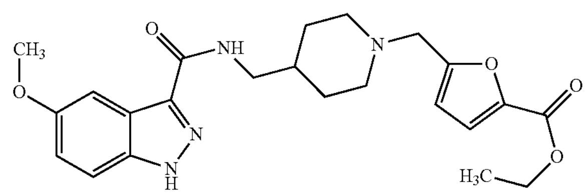 [SMILES: CCOC(=O)c1ccc(CN2CCC(CNC(=O)c3n[nH]c4ccc(OC)cc34)CC2)o1] |
| 24 | 5-{[4-({[(5-Methoxy-1H-indazol-3-yl)carbonyl]amino}methyl)piperidin-1-yl]methyl}furan-2-carboxylic acid | 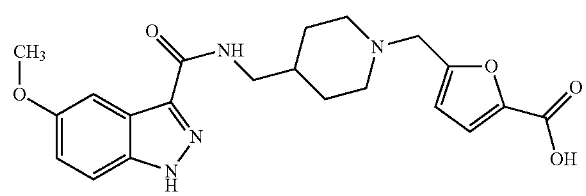 [SMILES: COc1ccc2[nH]nc(C(=O)NCC3CCN(Cc4ccc(C(=O)O)o4)CC3)c2c1] |
| 25 | N-[(1-{2-[(2R,6S)-2,6-dimethylmorpholin-4-yl]ethyl}piperidin-4-yl)methyl]-5-methoxy-1H-indazole-3-carboxamide | 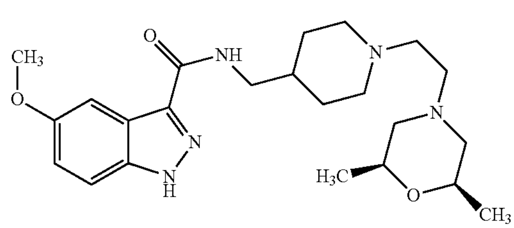 |

TABLE 1A-continued

| | IUPAC name | Structure |
|---|---|---|
| 26 | N-[(1-{3-[(2R,6S)-2,6-dimethylmorpholin-4-yl]propyl}piperidin-4-yl)methyl]-5-methoxy-1H-indazole-3-carboxamide | 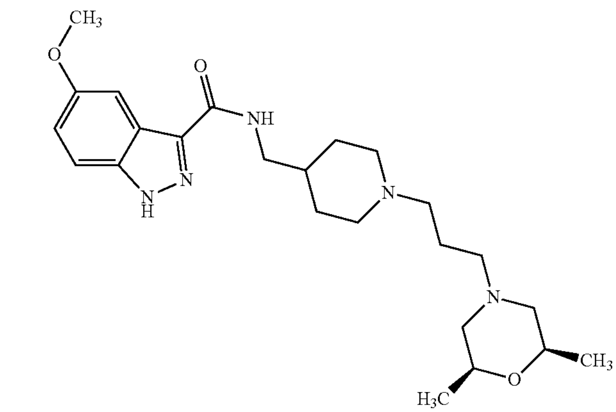 [SMILES: COc1ccc2[nH]nc(C(=O)NCC3CCN(CCCN4C[C@@H](C)O[C@@H](C)C4)CC3)c2c1] |
| 27 | 5-methoxy-N-({1-[2-(3-methylcyclohexyl)ethyl]piperidin-4-yl}methyl)-1H-indazole-3-carboxamide | 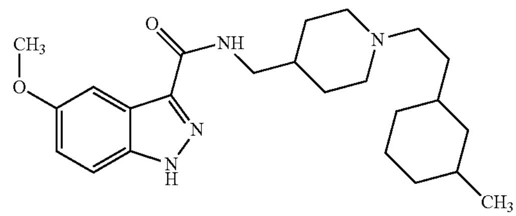 |
| 28 | 4-{[4-({[(5-methoxy-1H-indazol-3-yl)carbonyl]amino}methyl)piperidin-1-yl]methyl}pyridine-2-carboxylic acid | 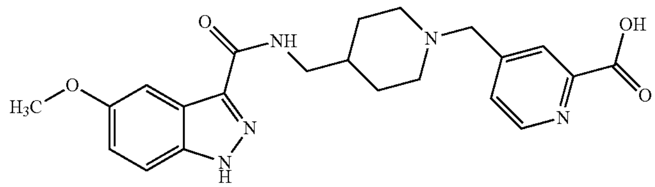 [SMILES: COc1ccc2[nH]nc(C(=O)NCC3CCN(Cc4ccnc(C(=O)O)c4)CC3)c2c1] |
| 29 | Sodium 5-{[4-({[(5-methoxy-1H-indazol-3-yl)carbonyl]amino}methyl)piperidin-1-yl]methyl}pyridine-2-carboxylate | 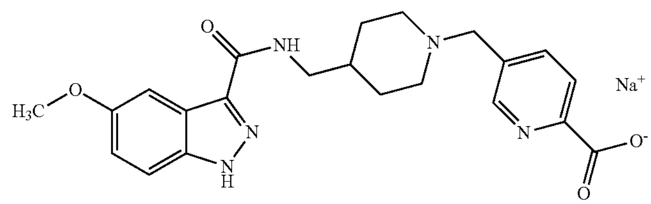 [SMILES: COc1ccc2[nH]nc(C(=O)NCC3CCN(Cc4ccc(C(=O)[O-])nc4)CC3)c2c1 ; [Na+]] |
| 30 | N-({1-[(5-carbamoyl-1,2,4-oxadiazol-3-yl)methyl]piperidin-4-yl}methyl)-5-methoxy-1H-indazole-3-carboxamide | 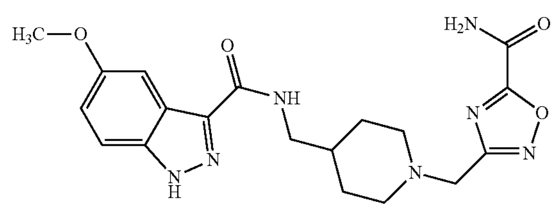 [SMILES: COc1ccc2[nH]nc(C(=O)NCC3CCN(Cc4noc(C(N)=O)n4)CC3)c2c1] |
| 31 | N-({1-[2-(4-nitrophenyl)ethyl]piperidin-4-yl}methyl)-1H-indazole-3-carboxamide hydrochloride | 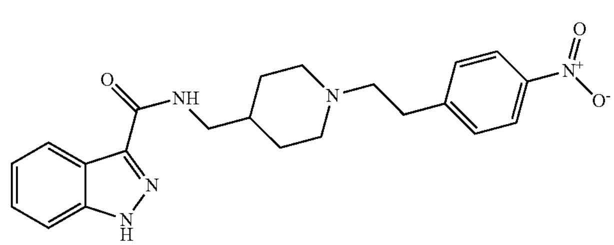 [SMILES: O=C(NCC1CCN(CCc2ccc([N+](=O)[O-])cc2)CC1)c1n[nH]c2ccccc12] |

Pharmacological Properties

The pharmacological properties of the compounds of formula (I) useful in the present invention were evaluated by the methods described in the following sections.

Test I—Activity on Human GSK-3β (Test In Vitro)

Activity on human GSK-3β was assessed using the following methods (according to Meijer et al., Chem. Biol., 2003-10:1255-1266).

In a first screening assay, compounds were tested in duplicate at a concentration of 10 μM.

Human recombinant enzyme GSK-3β was incubated for 90 minutes at 22° C. in the presence of compounds or vehicle in a reaction buffer containing ATP plus 100 nM unphosphorylated specific substrate peptide (Ulight-CFFKNIVTPRTPPPSQGK-amide) (SEQ ID NO: 1). Substrate phosphorylation was measured by LANCE technology (PerkinElmer, Conn., USA).

The results, reported in the following Table 4, are expressed as a percent of inhibition of control specific activity obtained in the presence of the test compounds (as % inhibition at 10 μM).

In a second assay, the same compounds were assayed at five concentrations ranging from 100 μM to 10 nM with ten-fold dilutions in duplicate. Compounds 1 to 7, 9, 11 and 13 to 26 were tested using the same first assay, compounds 8, 10, 12, and 27 to 31 were tested in another assay based on the binding and displacement of AlexaFluor® 647 labeled, ATP-competitive Kinase inhibitor scaffold using LanthaScreen™ TR-FRET technology Eu Kinase assay packet according to manufacturer's instruction (Life Technologies, Italy). The results of the two assays are comparable.

The $IC_{50}$ values (concentration causing a half maximal inhibition of control specific activity), reported in table 4, were determined by non-linear regression analysis of the inhibition curves generated with mean replicate values using Hill equation curve fitting.

TABLE 4

| Compound N° | % Inhibition [10 μM] | $IC_{50}$ [μM] |
|---|---|---|
| 1 | 94 | 0.35 |
| 2 | 91 | 0.56 |
| 3 | | 0.31 |
| 4 | | 0.64 |
| 5 | | 0.35 |
| 6 | | 0.40 |
| 7 | | 0.13 |
| 8 | | 0.17 |
| 9 | | 0.21 |
| 10 | | 0.31 |
| 11 | | 0.36 |
| 12 | | 0.01 |
| 13 | | 0.95 |
| 14 | | 0.23 |
| 15 | | 0.26 |
| 16 | | 0.36 |
| 17 | | 0.02 |
| 18 | | 0.30 |
| 19 | | 0.01 |
| 20 | | 0.02 |
| 21 | | 0.01 |
| 22 | | 0.21 |
| 23 | | 0.33 |
| 24 | | 0.40 |
| 25 | | 1.40 |
| 26 | | 2.10 |
| 27 | | 0.31 |
| 28 | | 0.45 |
| 29 | | 0.32 |
| 30 | | 0.31 |
| 31 | | 7.20 |

The results showed that the compounds 1 and 2 according to the present invention had good inhibitory activity in this assay: at 10 μM the % of inhibition is greater that 90% and the $IC_{50}$ is obtained with less than 0.60 μM of each compound.

Most of compounds 3 to 31 according to the present invention showed an $IC_{50}$ value lower than 1.00 μM. Some of them showed an $IC_{50}$ value at the lowest concentration of the assay (10 nM). The values of $IC_{50}$ higher than 1.00 μM obtained with compounds 25, 26 and 31 are still acceptable.

Test II—Selectivity on GSK-3β (Test In Vitro)

(a) Compound 1 was tested against a panel of 60 kinases in order to assess its selectivity. The assays were chosen taking into consideration the diversity of assay families.

Tested kinases were representative of following kinase sub-families:
protein-serine/threonine kinases;
protein-tyrosine kinases;
other kinases; and
atypical kinases.

Human recombinant kinases were incubated in the presence of specific peptide substrates plus ATP for different times (10, 15, 30, 60 or 90 minutes) at 22° C. Phosphorylated substrate was detected by LANCE or HTRF technology (CISBIO, MA, USA).

Compound 1 was tested at 10 μM in duplicate.

The results are expressed as a percent of inhibition of control specific activity obtained in the presence of the test compound 1 and are reported in the following Table 5.

TABLE 5

| Kinase Family | Kinase Sub-Family | Assay | % inhibition of control values for compound 1 |
|---|---|---|---|
| Protein-tyrosine kinases | RTK | c-Met kinase (h) | 0 |
| | RTK | EphA4 kinase (h) | 0 |
| | RTK | EphB2 kinase (h) | 0 |
| | RTK | EphB4 kinase (h) | 0 |
| | RTK | FGFR1 kinase (h) | 6 |
| | RTK | FGFR4 kinase (h) | 2 |
| | RTK | IGF1R kinase (h) | 5 |
| | RTK | IRK (h) (InsR) | 18 |
| | RTK | Ret kinase (h) | 1 |
| | RTK | TRKA (h) | 10 |
| | CTK | Abl kinase (h) | 0 |
| | CTK | JAK1 (h) | 0 |
| | CTK | JAK2 (h) | 0 |
| | CTK | Fyn kinase (h) | 13 |
| | CTK | Src kinase (h) | 0 |
| Protein serine/threonine kinases | CMGC | GSK3beta (h) | 92 |
| | CMGC | DYRK1a (h) | 63 |
| | CMGC | PCTAIRE1 kinase (h) | 87 |
| | CMGC | CDC2/CDK1 (h) (cycB) | 31 |
| | CMGC | CDK2 (h) (cycA) | 27 |
| | CMGC | CDK5/p35 (h) | 30 |
| | CMGC | ERK1 (h) | 35 |
| | CMGC | ERK2 (h) (P42mapk) | 33 |

TABLE 5-continued

| Kinase Family | Kinase Sub-Family | Assay | % inhibition of control values for compound 1 |
|---|---|---|---|
| | CMGC | p38alpha kinase (h) | 0 |
| | CMGC | p38gamma kinase (h) | 2 |
| | CMGC | p38delta kinase (h) | 12 |
| | CaMK | CHK1 (h) | 12 |
| | CaMK | AMPKalpha | 13 |
| | CaMK | CaMK4 (h) | 14 |
| | CaMK | DAPK1 (h) | 10 |
| | CaMK | DCAMKL1 (h) | 4 |
| | CaMK | Pim2 kinase (h) | 4 |
| | CaMK | MAPKAPK2 (h) | 0 |
| | CaMK | MNK2 (h) | 1 |
| | CaMK | PhKgamma 2 (h) | 6 |
| | CaMK | Pim1 kinase (h) | 2 |
| | CaMK | smMLCK (h) (MYLK) | 0 |
| | AGC | GRK3/BARK2 (h) (ADRBK2) | 8 |
| | AGC | Akt1/PKBalpha (h) | 7 |
| | AGC | MSK1 (h) | 8 |
| | AGC | PDK1 (h) | 8 |
| | AGC | RSK2 (h) | 3 |
| | AGC | PKA (h) | 0 |
| | AGC | PKCalpha (h) | 8 |
| | AGC | PKCbeta 1 (h) | 9 |
| | AGC | PKCgamma (h) | 0 |
| | CK1 | CK1alpha (h) | 15 |
| | STE | PAK1 (h) | 4 |
| | STE | HGK (h) (MAP4K4) | 17 |
| | STE | MEK1/MAP2K1 (h) | 25 |
| | STE | TAOK2 (TAO1) (h) | 41 |
| | TKL | DLK1 (h) (MAP3K12) | 10 |
| | TKL | IRAK4 (h) | 0 |
| Other kinases | — | IKKalpha (h) | 0 |
| | — | IKKepsilon (h) (IKBKE)4 | |
| | — | MYT1 kinase (h) | 1 |
| | — | NEK1 (h) | 1 |
| | — | NEK7 (h) | 9 |
| Atypical kinases | — | AurA/Aur2 kinase (h) | 1 |
| | — | AurB/Aur1 kinase (h) | 11 |
| | — | mTOR kinase (h) (FRAP1) | 0 |

Compound 1 was also assayed to determine the $IC_{50}$ values for three different kinases (PCTAIRE1, DYRK1a, and CDK2) in comparison to Gsk3β. The assay was conducted with the same method described above in test I, second assay. The results are summarized in the following Table 5A.

TABLE 5A

| Compound | IC50 [μM] Gsk3β | IC50 [μM] PCTAIRE1 | IC50 [μM] DYRK1a | IC50 [μM] CDK2 |
|---|---|---|---|---|
| 1 | 0.35 | 1.50 | 2.90 | 36.0 |

Results confirmed that compound 1 had an inhibitory activity on GSK-3β and higher affinity to GSK-3β when compared to the other kinases, showing a good selectivity profile. In fact, the $IC_{50}$ values of Table 5a showed a selectivity of compound 1 for Gsk3β better than that for PCTAIRE1, DYRK1a, and CDK2 kinases.

(b) Compounds 7, 12, 21 and 24 were tested against the same panel of 60 kinases under the same conditions described above for compound 1.

The results are expressed as a percent of inhibition of control specific activity obtained in the presence of the test compounds and are reported in the following Table 6.

TABLE 6

| Kinase Family | Kinase Sub-Family | Assay | Compound 7 | Compound 12 | Compound 21 | Compound 24 |
|---|---|---|---|---|---|---|
| Protein-tyrosine kinases | RTK | c-Met kinase (h) | — | — | 0 | 2 |
| | RTK | EphA4 kinase (h) | — | — | 2 | 0 |
| | RTK | EphB2 kinase (h) | — | — | 2 | 0 |
| | RTK | EphB4 kinase (h) | — | — | 3 | 0 |
| | RTK | FGFR1 kinase (h) | — | — | 13 | 0 |
| | RTK | FGFR4 kinase (h) | — | — | 0 | 4 |
| | RTK | IGF1R kinase (h) | — | — | 0 | 0 |
| | RTK | IRK (h) (InsR) | 0 | 0 | 0 | 3 |
| | RTK | Ret kinase (h) | — | — | 0 | 0 |
| | RTK | TRKA (h) | 1 | 5 | 4 | 1 |
| | CTK | Abl kinase (h) | — | — | 0 | 0 |
| | CTK | JAK1 (h) | — | — | 10 | 1 |
| | CTK | JAK2 (h) | — | — | 2 | 0 |
| | CTK | Fyn kinase (h) | — | — | 10 | 3 |
| | CTK | Src kinase (h) | 9 | 15 | 0 | 0 |
| Protein serine/threonine kinases | CMGC | GSK3beta (h) | 96 | 100 | 96 | 94 |
| | CMGC | DYRK1a (h) | 88 | 99 | 99 | 59 |
| | CMGC | PCTAIRE1 kinase (h) | 2 | 42 | 94 | 1 |
| | CMGC | CDC2/CDK1 (h) (cycB) | 6 | 77 | 99 | 10 |
| | CMGC | CDK2 (h) (cycA) | 48 | 96 | 100 | 36 |
| | CMGC | CDK5/p35 (h) | 21 | 87 | 98 | 16 |
| | CMGC | ERK1 (h) | 31 | 85 | 81 | 22 |
| | CMGC | ERK2 (h) (P42mapk) | 33 | 91 | 89 | 35 |
| | CMGC | p38alpha kinase (h) | — | — | 1 | 0 |
| | CMGC | p38gamma kinase (h) | — | — | — | — |
| | CMGC | p38delta kinase (h) | — | — | 35 | 4 |
| | CaMK | CHK1 (h) | — | — | 1 | 0 |
| | CaMK | AMPKalpha | — | — | 70 | 21 |
| | CaMK | CaMK4 (h) | — | — | 13 | 11 |

TABLE 6-continued

| Kinase Family | Kinase Sub-Family | Assay | Compound 7 | Compound 12 | Compound 21 | Compound 24 |
|---|---|---|---|---|---|---|
| | CaMK | DAPK1 (h) | — | — | 5 | 15 |
| | CaMK | DCAMKL1 (h) | — | — | 0 | 0 |
| | CaMK | Pim2 kinase (h) | — | — | 5 | 3 |
| | CaMK | MAPKAPK2 (h) | — | — | 0 | 0 |
| | CaMK | MNK2 (h) | — | — | 6 | 0 |
| | CaMK | PhKgamma 2 (h) | — | — | 0 | 0 |
| | CaMK | Pim1 kinase (h) | — | — | 10 | 2 |
| | CaMK | smMLCK (h) (MYLK) | 26 | 36 | — | — |
| | AGC | GRK3/BARK2 (h) (ADRBK2) | — | — | 4 | 0 |
| | AGC | Akt1/PKBalpha (h) | — | — | 0 | 0 |
| | AGC | MSK1 (h) | — | — | — | — |
| | AGC | PDK1 (h) | — | — | 0 | 0 |
| | AGC | RSK2 (h) | — | — | 20 | 1 |
| | AGC | PKA (h) | — | — | 3 | 0 |
| | AGC | PKCalpha (h) | — | — | 20 | 0 |
| | AGC | PKCbeta 1 (h) | — | — | 0 | 0 |
| | AGC | PKCgamma (h) | — | — | 0 | 0 |
| | CK1 | CK1 alpha (h) | — | — | 2 | 0 |
| | STE | PAK1 (h) | — | — | 4 | 1 |
| | STE | HGK (h) (MAP4K4) | 21 | 98 | 99 | 19 |
| | STE | MEK1/MAP2K1 (h) | 27 | 86 | — | — |
| | STE | TAOK2 (TAO1) (h) | 16 | 81 | 54 | 8 |
| | TKL | DLK1 (h) (MAP3K12) | — | — | 46 | 0 |
| | TKL | IRAK4 (h) | — | — | 18 | 1 |
| Other kinases | — | IKKalpha (h) | — | — | 5 | 2 |
| | — | IKKepsilon (h) (IKBKE) | — | — | 21 | 0 |
| | — | MYT1 kinase (h) | — | — | 0 | 0 |
| | — | NEK1 (h) | 0 | 30 | — | — |
| | — | NEK7 (h) | — | — | 5 | 3 |
| | — | AurA/Aur2 kinase (h) | — | — | 30 | 4 |
| | — | AurB/Aur1 kinase (h) | — | — | 10 | 0 |
| Atypical kinases | — | mTOR kinase (h) (FRAP1) | — | — | — | — |

Results confirmed that also compounds 7 and 24 had an inhibitory activity on GSK-3β and higher affinity to GSK-3β when compared to all other kinases, showing a good selectivity profile, and that compounds 12 and 21 had an inhibitory activity on GSK-3β and good affinity to GSK-3β when compared to most of other kinases of the same family and to the kinases of different families.

The invention claimed is:
1. A pharmaceutical composition, comprising:
an effective amount of a 1H-indazole-3-carboxamide according to formula (I), an addition salt of the 1H-indazole-3-carboxamide with a pharmaceutically acceptable organic or inorganic acid or base, or a prodrug of the 1H-indazole-3-carboxamide:

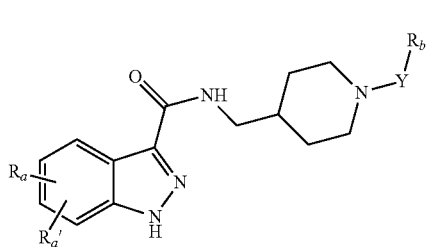

wherein:
each of $R_a$ and $R_a'$ is independently selected from a hydrogen atom, a halogen atom, a $C_1$-$C_6$ alkyl group, a $C_2$-$C_6$ alkenyl group, a $C_2$-$C_6$ alkynyl group, a $C_1$-$C_6$ alkoxy group, and an aliphatic or aromatic carbocyclic or heterocyclic ring having from 3 to 12 members, the alkyl, alkenyl, alkynyl, or alkoxy group being optionally substituted by at least one substituent selected from a halogen atom, a hydroxyl group, —$NH_2$, and a $C_1$-$C_3$ alkoxy group, and the ring being optionally substituted by at least one substituent selected from a halogen atom, a hydroxyl group, a $C_1$-$C_6$ alkyl group, a $C_1$-$C_6$ alkoxy group, —$NR_1R_2$, —C(O)OH, —C(O)$OR_1$, and —C(O)$NR_1R_2$;
Y is selected from a bond, a $C_1$-$C_6$ alkyl group, a $C_2$-$C_6$ alkenyl group, and a $C_2$-$C_6$ alkynyl group, the alkyl, alkenyl, or alkynyl group being optionally substituted by at least one substituent selected from a halogen atom, a hydroxyl group, —$NH_2$, and a $C_1$-$C_3$ alkoxy group;
$R_b$ is selected from furan, thiophene, thiazole, oxazole, and 1-oxa-2,4-diazole, and substituted by at least one substituent selected from a halogen atom, a hydroxyl group, a nitro group, —$CF_3$, a $C_1$-$C_6$ alkoxy group, a benzyloxy group, —$NHSO_2CH_3$, —$SO_2NH_2$, —Z—C(O)OH, and —Z—C(O)$OR_1$;
Z is a σ-bond or a ($C_1$-$C_3$)alkyl group; and
each of $R_1$ and $R_2$ is independently selected from a hydrogen atom, a $C_1$-$C_4$ alkyl group, a $C_2$-$C_4$ alkenyl group, a $C_2$-$C_4$ alkynyl group, and a phenyl group; and
at least one inert pharmaceutically acceptable excipient.

2. The pharmaceutical composition of claim 1, wherein each of $R_a$ and $R_a'$ is independently selected from a hydrogen atom, a chlorine atom, a bromine atom, an iodine atom, a $C_1$-$C_6$ alkyl group, a $C_1$-$C_6$ alkoxy group, and an aliphatic or aromatic carbocyclic or heterocyclic ring having from 4 to 10 members, the alkyl or alkoxy group being optionally substituted by at least one substituent selected from a halogen atom, a hydroxyl group, —$NH_2$, and a $C_1$-$C_3$ alkoxy group, and the ring being optionally substituted by at least one substituent selected from a halogen atom, a hydroxyl group, a $C_1$-$C_6$ alkyl group, a $C_1$-$C_6$ alkoxy group, —$NR_1R_2$, —C(O)OH, —C(O)$OR_1$, and —C(O)$NR_1R_2$.

3. The pharmaceutical composition of claim 1, wherein each of $R_a$ and $R_a'$ is independently selected from a chlorine atom, a bromine atom, a $C_1$-$C_6$ alkyl group, a $C_1$-$C_6$ alkoxy group, and an aliphatic or aromatic carbocyclic or heterocyclic ring having from 5 to 6 members, the alkyl or alkoxy group being optionally substituted by at least one substituent selected from a halogen atom, a hydroxyl group, —$NH_2$, and a $C_1$-$C_3$ alkoxy group, and the ring being optionally substituted by at least one substituent selected from a halogen atom, a hydroxyl group, a $C_1$-$C_6$ alkyl group, a $C_1$-$C_6$ alkoxy group, —$NR_1R_2$, and —C(O)OH.

4. The pharmaceutical composition of claim 3, wherein the aliphatic or aromatic carbocyclic or heterocyclic ring having from 5 to 6 members is selected from phenyl, pyridine, pyrimidine, pyrazine, pyridazine, pyrrole, furan, thiophene, oxazole, isoxazole, thiazole, isothiazole, 2H-pyran, cyclohexyl, cyclopenthyl piperidine, and piperazine.

5. The pharmaceutical composition of claim 1, wherein each of $R_a$ and $R_a'$ is independently selected from a bromine atom, a $C_1$-$C_3$ alkoxy group, and an aliphatic or aromatic carbocyclic or heterocyclic ring having 6 members, the alkoxy group being optionally substituted by at least one substituent selected from a halogen atom, a hydroxyl group, —$NH_2$, and a $C_1$-$C_3$ alkoxy group, and the ring being optionally substituted by at least one substituent selected from a halogen atom, a hydroxyl group, a $C_1$-$C_3$ alkyl group, a $C_1$-$C_3$ alkoxy group, —$NR_1R_2$, and —C(O)OH.

6. The pharmaceutical composition of claim 5, wherein the aliphatic or aromatic carbocyclic or heterocyclic ring having 6 members is selected from phenyl, pyridine, pyrimidine, pyrazine, pyridazine, 2H-pyran, cyclohexyl, piperidine, and piperazine.

7. The pharmaceutical composition of claim 5, wherein the aliphatic or aromatic carbocyclic or heterocyclic ring having 6 members is selected from phenyl, pyridine, pyrimidine, 2H-pyran, and cyclohexyl.

8. The pharmaceutical composition of claim 1, wherein Y is selected from a bond and a $C_1$-$C_6$ alkyl group optionally substituted by at least one substituent selected from a halogen atom, a hydroxyl group, —$NH_2$, and a $C_1$-$C_3$ alkoxy group.

9. The pharmaceutical composition of claim 1, wherein Y is a $C_1$-$C_6$ alkyl group.

10. The pharmaceutical composition of claim 1, wherein Y is a $C_1$-$C_3$ alkoxy group.

11. The pharmaceutical composition of claim 1, wherein $R_b$ is substituted by one or two substituents selected from a halogen atom, a hydroxyl group, a nitro group, —$CF_3$, a $C_1$-$C_3$ alkoxy group, and a benzyloxy group.

12. A method of treating a pathological state arising from uncontrolled activation and/or overexpression of GSK-3β comprising administering the pharmaceutical composition of claim 1 to a subject in need of such treatment, wherein the pathological state is selected from (i) an insulin-resistance disorder, (ii) a neurodegenerative disease, (iii) a mood disorder, (iv) a schizophrenic disorder, (v) a cancerous disorder, (vi) inflammation, (vii) a substance abuse disorder, and (viii) an epilepsy.

13. The method of claim 12, comprising treating an insulin-resistance disorder selected from type-2 diabetes, syndrome X, obesity, and polycystic ovary syndrome.

14. The method of claim 12, comprising treating a neurodegenerative disease selected from Parkinson's disease, Alzheimer's disease, Huntington's disease, and a spinal neurodegenerative disorder.

15. The method of claim 14, comprising treating a spinal neurodegenerative disorder selected from amyotrophic lateral sclerosis, multiple sclerosis, spinal muscular atrophy, and neurodegeneration due to spinal cord injury.

16. The method of claim 12, comprising treating a mood disorder selected from a bipolar disorder and a depressive disorder.

17. The method of claim 16, comprising treating a bipolar disorder selected from bipolar I, bipolar II, cyclothymia, and a bipolar disorder not otherwise specified (BD-NOS).

18. The method of claim 16, comprising treating a depressive disorder selected from major depressive disorder (MDD), atypical depression (AD), melancholic depression, psychotic major depression (PMD), catatonic depression, postpartum depression (PPD), seasonal affective disorder (SAD), dysthymia, and a depressive disorder not otherwise specified (DD-NOS).

19. The method of claim 12, wherein the pharmaceutical composition is used in treatment of an abuse disorder due to psychostimulants.

20. The method of claim 12, comprising treating a schizophrenic disorder selected from paranoid schizophrenia, disorganized schizophrenia, catatonic schizophrenia, simple schizophrenia, residual schizophrenia, and undifferentiated schizophrenia.

21. The method of claim 12, comprising treating a cancerous disorder selected from prostate cancer, pancreatic cancer, ovarian cancer, colon-rectal cancer, and MLL-associated leukaemia.

* * * * *